(12) United States Patent
Uhrich et al.

(10) Patent No.: US 9,144,579 B2
(45) Date of Patent: Sep. 29, 2015

(54) POLYESTERS AND METHODS OF USE THEREOF

(71) Applicant: Rutgers, The State University of New Jersey, New Brunswick, NJ (US)

(72) Inventors: Kathryn E. Uhrich, New Brunswick, NJ (US); Roselin Rosario-Melendez, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 135 days.

(21) Appl. No.: 13/970,220

(22) Filed: Aug. 19, 2013

(65) Prior Publication Data

US 2014/0050692 A1    Feb. 20, 2014

Related U.S. Application Data

(60) Provisional application No. 61/684,574, filed on Aug. 17, 2012.

(51) Int. Cl.
| | |
|---|---|
| *A61K 31/775* | (2006.01) |
| *A61K 31/765* | (2006.01) |
| *A61K 31/192* | (2006.01) |
| *C08G 63/00* | (2006.01) |
| *A61K 47/48* | (2006.01) |

(52) U.S. Cl.
CPC .............. *A61K 31/765* (2013.01); *A61K 31/192* (2013.01); *A61K 31/775* (2013.01); *A61K 47/482* (2013.01); *C08G 63/00* (2013.01)

(58) Field of Classification Search
None
See application file for complete search history.

(56) References Cited

U.S. PATENT DOCUMENTS

| | | |
|---|---|---|
| 2,607,799 A | 8/1952 | Weesner |
| 3,970,759 A | 7/1976 | Frankenfeld et al. |
| 4,062,855 A | 12/1977 | Allan et al. |
| 4,126,445 A | 11/1978 | Allan et al. |
| 4,164,560 A | 8/1979 | Folkman et al. |
| 4,298,595 A | 11/1981 | Parkinson et al. |
| 4,375,968 A | 3/1983 | Manhart |
| 4,414,203 A | 11/1983 | Cabardo, Jr. et al. |
| 4,591,496 A | 5/1986 | Cohen et al. |
| 4,612,302 A | 9/1986 | Szabo et al. |
| 4,684,620 A | 8/1987 | Hruby et al. |
| 4,757,128 A | 7/1988 | Domb et al. |
| 4,792,598 A | 12/1988 | Ziegast |
| 4,857,311 A | 8/1989 | Domb et al. |
| 4,868,274 A | 9/1989 | Gupta et al. |

(Continued)

FOREIGN PATENT DOCUMENTS

| | | |
|---|---|---|
| AU | 750424 | 3/2003 |
| CA | 2393676 | 7/2002 |

(Continued)

OTHER PUBLICATIONS

Aebischer, P., et al., "Basic fibroblast growth factor released from synthetic guidance channels facilitates peripheral nerve regeneration across long nerve gaps", *Journal of Neuroscience Research*, 23(2), 282-289, (Jul. 1989).

(Continued)

*Primary Examiner* — Brian Gulledge
(74) *Attorney, Agent, or Firm* — Viksnins Harris & Padys PLLP

(57) ABSTRACT

The invention provides polymers and methods for the treatment of pain and inflammation.

19 Claims, 11 Drawing Sheets

A.

B.

(56) References Cited

U.S. PATENT DOCUMENTS

| | | |
|---|---|---|
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,997,904 A | 3/1991 | Domb |
| 4,999,417 A | 3/1991 | Domb |
| 5,032,216 A | 7/1991 | Felten |
| 5,082,925 A | 1/1992 | Shalaby et al. |
| 5,160,745 A | 11/1992 | DeLuca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,901,705 B2 | 3/2011 | Roby et al. |
| 7,985,415 B2 | 7/2011 | Giroux |
| 8,017,714 B2 | 9/2011 | Uhrich |
| 8,088,405 B2 | 1/2012 | Uhrich et al. |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 2001/0046476 A1 | 11/2001 | Plochocka |
| 2003/0035787 A1 | 2/2003 | Uhrich et al. |
| 2003/0059469 A1 | 3/2003 | Uhrich et al. |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2007/0014832 A1 | 1/2007 | Uhrich et al. |
| 2007/0098800 A1 | 5/2007 | Giroux et al. |
| 2007/0196417 A1 | 8/2007 | Uhrich et al. |
| 2010/0152410 A1 | 6/2010 | East et al. |
| 2010/0291180 A1 | 11/2010 | Uhrich et al. |
| 2010/0310498 A1 | 12/2010 | Kanamathareddy et al. |
| 2011/0022161 A1 | 1/2011 | Uhrich et al. |
| 2011/0243884 A1* | 10/2011 | O'Shea et al. ............ 424/78.36 |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |
| 2014/0271864 A1 | 9/2014 | Uhrich et al. |

FOREIGN PATENT DOCUMENTS

| | | |
|---|---|---|
| DE | 288311 | 3/1991 |
| DE | 0288387 | 3/1991 |
| EP | 0246341 | 11/1987 |
| EP | 0483429 | 5/1992 |
| EP | 0498283 | 8/1992 |
| EP | 0580386 | 1/1994 |
| FR | 2839451 | 11/2003 |
| JP | 51-134729 | 11/1976 |
| JP | 53-082743 | 7/1978 |
| JP | 56-007716 | 1/1981 |
| JP | 6255797 | 12/1985 |
| JP | 61186309 | 8/1986 |
| JP | 06-328857 | 11/1994 |
| JP | 07-149044 | 6/1995 |
| NL | 9000237 | 8/1991 |
| WO | WO 90/09779 | 9/1990 |
| WO | WO 91/09831 | 7/1991 |
| WO | WO 91/18940 | 12/1991 |
| WO | WO 97/39738 | 10/1997 |
| WO | WO 97/44016 | 11/1997 |
| WO | WO 97/49385 | 12/1997 |
| WO | WO 98/36013 | 8/1998 |
| WO | WO 99/12990 | 3/1999 |
| WO | WO 99/29885 | 6/1999 |
| WO | WO 99/36107 | 7/1999 |
| WO | WO 00/66730 | 11/2000 |
| WO | WO 01/028492 | 4/2001 |
| WO | WO 01/041753 | 6/2001 |
| WO | WO 02/009767 | 2/2002 |
| WO | WO 02/009768 | 2/2002 |
| WO | WO 02/009769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |
| WO | WO 2012/139015 | 10/2012 |
| WO | WO 2014/194055 | 12/2014 |

OTHER PUBLICATIONS

Anastasiou, T.J., "Novel, Degradable Polyanhydrides", *25th Annual Meeting Transactions of the Society for Biomaterials*, Abstract, 79, (1999).

(56) References Cited

OTHER PUBLICATIONS

Anastasiou, T.J., "Novel Polyanhydrides with Enhanced Thermal and Solubility Properties", *Macromolecules*, 33(17), 6217-6221, (2000).
Anastasiou, T.J., "Synthesis of Novel, Degradable Polyanhydrides Containing Para-Aminosalicylic Acid as Drug Delivery Devices for Tuberculosis Treatment", *Polymer Preprints*, 41(2), 1366-1367, (Aug. 2000).
Arredondo et al., Effects of Linkers Substitution on Salicylic Acid-derived Poly(anhydride-esters), website of Rutgers, the State University of New Jersey, 16 pages (2001).
Arica et al., "In vitro and in vivo studies of ibuprofen-loaded biodegradable alginate beads", *J. Microencapsulation 22*, 153-165 (2005).
Attawia, M.A., "Biocompatibility Testing of Poly(anhydride-co-imides) Containing Pyromellitylimidoalanine", *The 21st Annual Meeting of the Society for Biomaterials*, Abstract, 222, (Apr. 5-9, 1994).
Attawia, M.A., "Cytotoxicity testing of poly(anhydride-co-imides) for orthopedic applications", *Journal of Biomedical Materials Research*, 29(10), 1233-1240, (1995).
Attawia, M.A., "In vitro bone biocompatibility of poly(anhydride-co-imides) containing pyromellitylimidoalanine", *Journal of Orthopedic Research*, 14(3), 445-454, (1996).
Attawia, M.A., "The Long Term Osteoblast Response to Poly(anhydride-co-imides): A New Degradable Polymer for Use in Bone", *Proceedings of the Fifth World Biomaterials Congress*, Toronto, Canada, 113, (1996).
Attawia, M.A., "Proliferation, Morphology, and Protein Expression by Osteoblasts Cultured on Poly(anhydride-co-amides)", *Journal of Biomedical Materials Research*, 48(3), 322-327, (1999).
Attawia, M.A., "Regional drug delivery with radiation for the treatment of Ewing's sarcoma—in vitro development of a taxol release system", *Journal of Controlled Release*, 71, 193-202 (2001).
Babazadeh, "Synthesis and study of controlled release of ibuprofen from the new acrylic type polymers" *Int. J. Pharm. 316*, 68-73 (2006).
Babazadeh "Design, synthesis and in vitro evaluation of vinyl ether type polymeric prodrugs of ibuprofen, ketoprofen and naproxen", *Int. J. Pharm. 356*, 167-173 (2008).
Beaton, M.L., "Synthesis of a novel poly(anhydride-ester)", *The Rutgers Scholar-An Electronic Bulletin of Undergraduate Research*, 3, 1-7, (2001), http://www.scils.rutgers.edu/~weyang/ejournal/volume03/beatuhri/beatuhri.htm.
Bedell, C., "Processing and Hydrolytic Degradation of Aromatic, Ortho-Substituted Polyanhydrides", *Journal of Applied Polymer Science*, 80, 32-38, (2001).
Borovac et al., "Release of ibuprofen from beads for embolization: in vitro and in vivo studies", *J. Controlled Release 115*, 266-274 (2006).
Borzacchiello et al., "Synthesis and Characterization of Saturated and Unsaturated Poly(alkylene tartrate)s and Further Cross-linking", *J. Bioact. Compat. Polym. 15*, 60-71 (2000).
Bozdag et al., "Release of ibuprofen from beads for embolization: in vitro and in vivo studies", *J. Controlled Release 115*, 266-274 (2006).
Brambley, D., et al., "Microlithography: an overview", *Advanced Materials for Optics and Electronics*, 4(2), 55-74, (Mar.-Apr. 1994).
Branch, D.W., "Microstamp patterns of biomolecules for high resolution neuronal networks", *Medical & Biological Engineering & Computing*, 36(1), 135-41, (Jan. 1998).
Brown, J.P., "A Polymeric Drug for Treatment of Inflammatory Bowel Disease", *Journal of Medicinal Chemistry*, 26(9), 1300-1307, (1983).
Brown, L., et al., "Transderrnal delivery of drugs", *Annual Review of Medicine*, 39, 221-9, (1988).
Campo, C.J., "Polyanhydrides: the effects of ring substitution changes on polymer properties", *Polymer Bulletin*, 42, 61-68, (1999).
Carbone et al., "Design and Synthesis of Fast-Degrading Poly(anhydride-esters)", *Macromol. Rapid Commun.*, 30, 1021-1026 (2009).

Castelli et al. "Comparative study of 'in vitro' release of anti-inflammatory drugs from polylactide-co-glycolide microspheres", *Int. J. Pharm. 176*, 85-98 (1998).
Chafi, N., "Dosage Form with Salicylic Acid Attached to the Polyanhydride Polymer Dispersed in an Eudragit Matrix", *International Journal of Pharmaceutics*, 52, 203-211, (1989).
Chatterjee, R., et al., "Mechanism for the Increase in Solubility of Deoxyhemoglobin S due to Cross-Linking the Beta Chains Between Lysine-82 Beta1 and Lysine-82 Beta 2", *Biochemistry*, 21, 5901-5909, (1982).
Chen, G., "Effect of protein and cell behavior on pattern-grafted thermoresponsive polymer", *Journal of Biomedical Materials Research*, 42(1), 38-44, (Oct. 1998).
Conix, A., "New High-Melting Fibre-Forming Polymers", *Die Makromolekulare Chemie*, XXIX, 76-78, (1957).
Conix, A., "Aromatic Polyanhydrides, a New Class of High Melting Fiber-Forming Polymers", *Journal of Polymers Science*, XXIX, 343-353, (1958).
Conix, A., "Poly [1,3-bis (p carboxyphenoxy)—Propane anhydride]", *Macromolecular Synthesis*, 2, 95-99, (1996).
Cotlier, "Distribution of salicylate in lens and intraocular fluids and its effect on cataract formation", *American Journal of Medicine*, 74 (6A), 83-90 (1983).
Cotlier, "Senile Cataracts: Evidence for Acceleration by Diabetes and Deceleration by Salicytate", *Canadian Journal of Ophthalmology*, 16(3), 113-118 (1981).
Davaran et al. "Hydrophilic copolymers prepared from acrylic type derivatives of ibuprofen containing hydroyzable thioester bond" (1998). *Eur. Polym. J. 34* (2), 187-192 (1998).
Davaran, S., "Release of 5-amino Salicylic Acid from Acrylic Type Polymeric Prodrugs Designed for Colon-specific Drug Delivery", *Journal of Controlled Release*, 58(3), 279-287, (1999).
Davies, M.C., "The Analysis of the Surface Chemical Structure of Biomedical Aliphatic Polyanhydrides Using SPX and ToF-SIMS", *Journal of Applied Polymer Science*, 42, No. 6, New York, US, 1597-1605, (Mar. 20, 1991).
Debolt et al. "L-tartaric acid synthesis from vitamin C in higher plants", *Proc. Natl. Acad. Sci. 103*, 5608-5613 (2006).
Delamarche, E., et al., "Patterned delivery of immunoglobulins to surfaces using microfluidic networks", *Science*, 276(5313), 779-781, (May 2, 1997).
Dewez, J.L., et al., "Adhesion of mammalian cells to polymer surfaces: from physical chemistry of surfaces to selective adhesion on defined patterns", *Biomaterials*, 19(16), 1441-1445, (Aug. 1998).
Domb, A.J., "Polyanhydrides. I. Preparation of High Molecular Weight Polyanhydrides", *Journal of Polymer Science: Part A: Polymer Chemistry*, 25, 3373-3386, (1987).
Domb, A.J., "Synthesis and Characterization of Biodegradable Aromatic Anhydride Copolymers", *Macromolecules*, 25, 12-17, (1992).
Dontha, N, "Generation of biotin/avidin/enzyme nanostructures with maskless photolithography", *Analytical Chemistry*, 69(14), 2619-25, (Jul. 15, 1997).
Dukovic, G., "Novel degradable poly(anhydride-esters) for controlled drug release", *The Rutgers Scholar-An Electronic Bulletin of Undergraduate Research*, 1, 1-10, (1999), http://www.scils.rutgers.edu/~weyang/ejournal/volume01/uhriduko/uhriduko.htm.
Dugaiczyk et al., "Nucleotide sequence and the encoded amino acids of human serum albumin mRNA", *Proc. Natl Acad Sci*, vol. 79, 71-75 (1982).
Erdmann, L., "Polymer Prodrugs with Pharmaceutically Active Degradation Products", *Polymer Preprints*, 38(2), 570-571, (1997).
Erdman et al., "Synthesis and Characterization of a Polymeric Prodrug", *Proceedings of the American Chemical Society Division of Polymeric Materials: Science and Engineering*, 78, Abstract Spring Meeting, Dallas, TX, pp. 194, (Apr. 1998).
Erdmann, L., et al., Chapter 5, "Polymeric Prodrugs: Novel Polymers with Bioactive Components", *In: Tailored Polymeric Materials for Controlled Delivery Systems*, I. McCulloh, et al., (Editors), ACS Symposium Series 709, Developed from a symposium sponsored by the Division of Polymer Chemistry at the 214th National Meeting of the American Chemical Society, Las Vegas, Nevada, Sep. 7-11, 1997, American Chemical Society: Washington, D.C., 83-91, (1998).

(56) References Cited

OTHER PUBLICATIONS

Erdmann, L., "Polymeric Prodrugs: Novel Polymers for Delivery of Salicylic Acid", *Annals of Biomedical Engineering*, 26 (Suppl. 1), Abstract No. PB.26, Annual Fall Meeting, S-124, (1998).
Erdmann, L., "Polymeric Salicylic Acid: In Vitro and In Vivo Degradation", *Polymer Preprints*, 224-225, (1998).
Erdmann, L., "Degradable poly(anhydride ester) implants: effects of localized salicylic acid release on bone", *Biomaterials*, 21(24), 2507-2512, (2000).
Erdmann, L., "Synthesis and degradation characteristics of salicylic acid-derived poly(anhydride-esters)", *Biomaterials*, 21(19), 1941-1946, (Oct. 2000).
Fernandez-Carballido et al., "I Biodegradable ibuprofen-loaded PLGA microspheres for intraarticular administration. Effect of Labrafil addition on release in vitro" *Int. J. Pharm.* 279, 33-41 (2004).
Gallardo et al. "NSAIDs bound to methacrylic carriers: microstructural characterization and in vitro release analysis", *J. Controlled Release 71*, 127-140 (2001).
Giammona, G., "Polymeric Prodrugs alpha beta poly-hyroxyethyl-d1-aspartamide as macromolecular carrier for some non-steroidal anti-inflammatory agents", *Abstracts from Database BIOSIS Online, Biosciences Information Service*, Philadelphia, PA, Original Publication from the International Journal of Pharmaceutics (Amsterdam), 1 page (1989).
Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, 55-62, (1989).
Gouin, S., et al., "New Polyanhydrides Made from a Bile Acid Dimer and Sebacic Acid: Synthesis, Characterization and Degradation", *Macromolecules*, 33, 5379-5383, (2000).
Herbert, C.B., "Micropatterning gradients and controlling surface densities of photoactivatable biomolecules on self-assembled monolayers of oligo(ethylene glycol) alkanethiolates", *Chemistry & Biology*, 4(10), 731-7, (Oct. 1997).
Ibim, S., "Controlled Release Based on Poly(anhydride-co-imides)", *Proc. Intern. Symp. Control. Rel. Bioact. Mater.*, 22, 2 pgs, (1995).
Ibim, S.M., "Poly(anhydride-co-imides): In Vivo Biocompatibility in a rat model", *Biomaterials*, 19(10), 941-951, (1998).
Ibim, S.E., "Preliminary in vivo report on the osteocompatibility of poly(anhydride-co-imides) evaluated in a tibial model.", *Journal of Biomedical Material Research*, 43(4), 374-379, (Winter 1998).
Ito, Y., "Micropatterned immobilization of epidermal growth factor to regulate cell function", *Bioconjugate Chemistry*, 9(2), 277-82, (Mar.-Apr. 1998).
Jain et al. "Role of polyanhydrides as localized drug carriers", *J. Controlled Release 103*, 541-563 (2005).
James, C.D., "Patterned Protein Layers on Solid Substrates by Thin Stamp Microcontact Printing", *Langmuir*, 14(4), 741-744, (1998).
Jeffcoat, "The Effect of Systemic Flurbiprofen on Bone Supporting Dental Implants", *Journal of American Dental Associate*, 126, 305-311 (1995).
Jiang, H.L., "Synthesis, Characterization and In Vitro Degradation of a New Family of Alternate Poly(ester-anhydrides) Based on Aliphatic and Aromatic Diacids", *Biomaterials*, 22(3), 211-218, (2001).
Jucker, M., et al., "Fetal rat septals cells adhere to and extend processes on basement membrane, laminin, and a synthetic peptide from the laminin A chain sequence", *Journal of Neuroscience Research*, 28(4), 507-17, (Apr. 1991).
Juais et al., "Isosorbide Polyesters from Enzymatic Catalysis", *Macromolecules*, 43, 10315-10319 (2010).
Khan et al. "Synthesis, pharmacological activity and hydrolytic behavior of glyceride prodrugs of ibuprofen", *Eur. J. Med. Chem.* 40, 371-376 (2005).
Kleinfeld, D., "Controlled outgrowth of dissociated neurons on patterned substrates", *Journal of Neuroscience*, 8(11), 4098-120, (Nov. 1998).

Krogh-Jespersen, E., "Synthesis of a Novel Aromatic Polyanhydride Containing Aminosalicylic Acid", *Polymer Preprints*, 41(1), 1048-1049, (2000).
Lamidey et al., "A Convenient Synthesis of the Echinacea-Derived Immunostimulator and HIV-1 Integrase Inhyibitor (--)-(2R,3R)-Chicoric Acid", *Hely. Chico. Acta 85*, 2328-2334 (2002).
Langer, R., "New Methods of Drug Delivery", *Science*, 249(4976), 1527-1533, (Sep. 1990).
Laurencin, C.T., "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, C.T., "Poly(anhydrides-co-imides): In Vivo Biocompatibility Study", *23rd Annual Meeting of the Society for Biomaterials*, New Orleans, LA, 483, (1997).
Laurencin, C.T., "The Biocompatibility of Poly(anhydride-co-imides): High Strength Polymers for Controlled Drug Delivery", *Proc. 24th Int'l Symp. Control. Rel. Bioact. Mater.*, 973-974, (1997).
Laurencin, et al., "The controlled delivery of radiosensitizers: taxol treatment for Ewing Sarcoma", *Proceedings of the $25^{th}$ Int'l Symp. Control. Rel. Bioact. Mater.*, pp. 236-237, (1998).
Liso et al. "Antinociceptive and antipyretic properties of a new conjugated ibuprofen-methacrylic polymeric controlled delivery system", *J. Controlled Release 33*, 429-436 (1994).
Longer, M.A., "Sustained-Release Drug Delivery Systems", *Remington's Pharmaceutical Sciences*, 18th Edition, Chapter 91, 1676-1693, (1990).
Macedo, B., et al., "The in vivo Response to a Bioactive Biodegradable Polymer", *Journal of Dental Research*, 78, Abstract No. 2827, 459, (1999).
Macedo, B., "The In Vivo Response to Bioactive Polyanhydride Monofilament", *Journal of Dental Research*, 79 (Abstract No. 3872), 627, (2000).
March, Advanced organic chemistry: reactions, mechanisms, and structure, $4^{th}$ Edition, New York: Willey, 419-437 (1992).
Pillai et al. "Polymers in drug delivery", *Curr. Opin. Chem. Biol. 5*, 447-451 (2001).
Pinther, P., "Synthesis of Polyanhydrides Containing Ester Groups", *Die Makromolekulare Chemie, Rapid Communications*, 11(8), 403-408, (Aug. 1990).
Prudencio, A., "Biodegradable Polyanhydrides for Controlled Drug Release", Dissertation submitted to the Graduate School—New Brunswick, Rutgers, The State University of New Jersey, 228 pages (Oct. 2006).
Prudencio, A., et al., "A Novel Approach for Incorporation of Mono-Functional Bioactive Phenols into Polyanhydrides", *Macromolecular Rapid Communications*, 30, 1101-1108, 2009.
Reynolds, et al., "Non-steroidal anti-inflammatory drug (NSAID)-derived poly(anhydride-esters) in bone and periodontal regeneration", *Current Drug Delivery*, 4(3), 233-239 (Jan. 1, 2007).
Rosario-Melendez et al., "Ibuprofen- and Naproxen-based Polyesters: Synthesis and Characterization", Poster, American Chemical Society National Meeting, Philadelphia, PA, 1 page (Aug. 19-23, 2012).
Rosario-Melendez et al., "Ibuprofen- and naproxen-based poly(anhydride-esters): Synthesis and characterization of polymer precursors", Abstract, PMSE, American Chemical Society National Meeting, Philadelphia, PA, 1 page (Jun. 2012).
Rosario-Melendez et al., "Ibuprofen- and Naproxen-based Poly(anhydride-esters): Synthesis and Characterization of Polymer Precursors", *Polym. Mat. Sci. Eng.*, 107, 443-444 (Aug. 1, 2012).
Rosario-Melendez et al., "Biodegradable polyesters containing ibuprofen and naproxen as pendant groups", *Biomacromolecules 14* (10), 3542-3548 (2013).
Schacht, E., "Polymers for Colon Specific Drug Delivery", *Journal of Controlled Release*, 39, 327-338, (1996).
Schwach et al., "Stannous octoate versus zinc-initiated polymerization of racemic lactide: Effect of configurational structures", *Polym. Bull.* 32, 617-623 (1994).
Schwach et al. "Influence of polymerization conditions on the hydrolytic degradation of poly(DL-lactide) polymerized in the presence of stannous octoate or zinc-metal" *Biomaterials* 23, 993-1002 (2002).

(56) References Cited

OTHER PUBLICATIONS

Schmalenberg, K., "Microlithographic patterning of polymer substrates for directed neuronal", *Polymeric Materials Science Engineering*, 81, Fall Meeting, Aug. 22-26, 1999, New Orleans, LA., 97, (1999).
Schmalenberg, K., "Patterned Polymer Substrates for directing Neuronal Growth", *ACS Regional Mid-Atlantic Research Meeting*, (1999).
Schmalenberg, K., "Patterning of polymer substrates for directed neuronal growth studies", *Laboratory for Surface Modification*, (Mar. 18, 1999).
Schmalenberg, K., "Thin Stamp Microcontact Patterned Printing of Protein Layers on Polymer Substrates", *Transactions: Twenty-Fifth Annual Meeting of the Society for Biomaterials*, Apr. 28-May 2, 1999.
Seidel, J.O., "Erosion of Poly(anhydride-co-imides): A Preliminary Mechanistic Study", *J. Appl. Polym. Sci.*, 62(8), 1277-1283, (1996).
Shen, E., "Morphological Characterization of Erodible Polymer Carriers for Drug Release", *Proc. 26th Int'l Symp. Control. Rel. Bioact. Mater.*, 717-718, (1999).
Spargo, B.J., et al., "Spatially controlled adhesion, spreading, and differentiation of endothelial cells on self-assembled molecular monolayers", *Proceedings of the National Academy of Science USA*,91(23), 11070-11074, (Nov. 8, 1994).
Sparks, et al., "Life after Union: Polymers-R-Us", Presentation at Union College, 40 pages (2007).
St. John, P.M., "Diffraction-based cell detection using a microcontact printed antibody grating", *Analytical Chemistry*, 70(6), 1108-11, (Mar. 15, 1998).
Storey et al. "Kinetics and Mechanism of the Stannous Octoate-Catalyzed Bulk Polymerization of epsilon-caprolactone", *Macromol.* 35, 1504-1512 (2002).
Swinyard, "Pharmaceutical Necessities", In: *Remington's pharmaceutical sciences* by Joseph P. Remington; Alfonso R. Gennaro, Easton, PA.: Mack Pub. Co.: ISBN:0912734043, 1286-1329 (1990).
Tashiro, K., et al., "A synthetic peptide containing the IKVAV sequence from the A chain of laminin mediates cell attachment, migration, and neurite outgrowth", *Journal of Biological Chemistry*, 264(27), 16174-82, (Sep. 25, 1989).
The Merck Index, Twelfth Edition, Merck & Co., Inc. Ed. By S. Budavari et al., p. 1090, compound 6435 (1996).
Thompson et al., "Evaluation of ibuprofen-loaded microspheres prepared from novel copolyesters", *Int. J. Pharm. 329*, 53-61 (2007).
Thompson et al., "Preparation and evaluation of microspheres prepared from novel polyester-ibuprofen conjugates blended with non-conjugated ibuprofen", *J. Microencapsulation* 26 (8), 676-683 (2009).
Uhrich, K.E., "Synthesis and Characterization of poly(anhydride co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA, 239-240, (1994).
Uhrich, K.E., "Synthesis and Characterization of Degradable poly(anhydride-co-imides)", *Macromolecules*, 28(7), 2184-2193, (1995).
Uhrich, K.E., "Degradation of poly(anhydride-co-imides): Novel Polymers for Orthopedic Applications", *Mat. Res. Soc. Symp. Proc.*, 394, 41-46, (1995).
Uhrich, K.E., "In Vitro Degradation Characteristics of Poly(anhydride-imides) Containing Pyromellitylimidoalanine", *J. Appl. Polymer Sci., Part A, Polym. Chem.*, 34(7), 1261-1269, (1996).
Uhrich, K.E., "In Vitro Degradation Characteristics of Poly(anhydride-imides) Containing trimellitylimidoglycine", *J. Appl. Polymer. Sci.*, 63(11), 1401-1411, (1997).
Uhrich, K.E., "Chemical Changes during in vivo degradation of poly(anhydride-imide) matrices", *Biomaterials*, 19(22), 2045-2050, (1998).
Uhrich, K.E., "Poly(anhydride-ester) Degradation: Mechanical Changes and Correlation to Antibiotic Release", *American Chemical Society, Abstracts of Papers*, Part 2, Abstract No. 121, 221$^{st}$ ACS National Meeting, San Diego, CA, Abstract 121, (2001).
Uhrich, K.E., "Synthesis of Aminosalicylate-based polyanhydride Prodrugs: Esters, Amides, and Azos", *American Chemical Society, Abstracts of Papers*, Part 2, Abstract No. 407, 222nd ACS National Meeting, Chicago, IL, Abstract 407, (2001).
Uhrich, K.E., "Designing Polymers for Biomedical Applications", Presentation at Division of Engineering & Applied Science, Harvard University, Cambridge, MA, 50 pages (2002).
Woo et al., "Synthesis and characterization of a novel biodegradable antimicrobial polymer", *Biomaterials*, 21, 1235-1246 (2000).
Woo, G.L., "Biological Characterization of a Novel Biodegradable Antimicrobial Polymer Synthesized with Fluoroquinolones", *J. Biomed. Mater. Res.* 59, 35-45, (2002).
Yazdi et al., "Effects of non-steroidal anti-inflammatory drugs on demineralized bone-induced bone formation", *Journal of Periodontal Research*, 27(1), 28-33, (Jan. 1992).
Yoda, N., "Synthesis of polyanhydrides. XII. Crystalline and high melting of polyamidepolyanhydride methylenebis(p-carboxybhenyl)amide", *Journal of Polymer Science*, 1, 1323-1338, (1963).
Zaugg, R.H., et al., "Modification of Hemoglobin with Analogs of Aspirin", *The Journal of Biological Chemistry*, 255(7), 2816-2821, (1980).

\* cited by examiner

A.

B.

POLYESTERS AND METHODS OF USE THEREOF

CROSS-REFERENCE TO RELATED APPLICATION(S)

This application claims priority from U.S. Provisional Application No. 61/684,574, filed Aug. 17, 2012, which application is herein incorporated by reference.

GOVERNMENT FUNDING

The invention described herein was made with government support under Grant Numbers NIH 5 RO1DE0132070 and NIH 1 RO1DE019926 awarded by the National Institutes of Health. The United States Government has certain rights in the invention.

BACKGROUND OF THE INVENTION

Propionic acid derivative non-steroidal anti-inflammatories (NSAIDs) (e.g., ibuprofen and naproxen) are commonly used to treat pain, inflammation and swelling (e.g., associated with rheumatoid arthritis and osteoarthritis). To treat these long-lasting symptoms, administration of high and repeated systemic doses is often required. As a result, severe gastrointestinal (GI) side effects (e.g., stomach ulceration, bleeding, and perforation) occur because the drug is distributed throughout the body to target and non-target sites. Drug delivery systems have been developed to control the drug release, thereby prolonging the duration of the drug effect. However, these systems suffer from major disadvantages such as low drug-loadings, uncontrolled (i.e., burst) release of the drug, and use of non-biodegradable materials.

Accordingly, new methods and compositions to treat pain and inflammation are needed.

SUMMARY OF THE INVENTION

Accordingly, certain embodiments of the invention provide a polyester comprising one or more groups of formula (I):

wherein A is a $C_1$-$C_8$ methylene chain that is covalently linked to one or more residues of a non-steroidal anti-inflammatory; and L is a $C_2$-$C_{10}$ branched or straight chain alkyl or is a residue of formula (III):

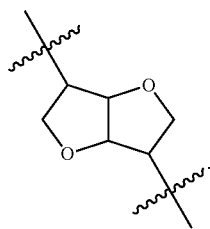

Certain embodiments of the present invention provide a pharmaceutical composition comprising a polyester as described herein and a pharmaceutically acceptable carrier.

Certain embodiments of the present invention provide a method to treat pain or inflammation in a mammal (e.g., a human), comprising administering a polyester as described herein to the mammal.

Certain embodiments of the present invention provide processes and intermediates disclosed herein that are useful for preparing a polymer of the invention and are described herein (e.g. the Examples). The intermediates described herein may have therapeutic activity, and therefore, may also be used for the treatment of pain or inflammation.

DETAILED DESCRIPTION

Figure 1:
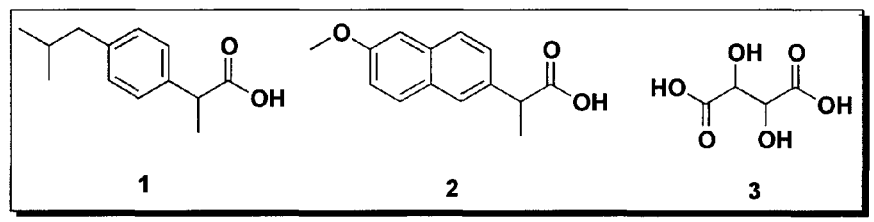
FIG. 1. (A) Chemical structures of ibuprofen (1), naproxen (2), and tartaric acid (3). (B) Synthesis of ibuprofen- and naproxen-protected diacids (5a and 5b, respectively) by coupling of the drug's (1 or 2) carboxylic acids to the hydroxyl groups of the dibenzyl protected tartaric acid (4). Deprotection to yield the diacids (6a and 6b) was performed using two different hydrogenation methods and synthesis of ibuprofen- and naproxen-tartaric polymers (7a and 7b) was performed using tin (II) 2-ethylhexanoate as catalyst. While this synthetic scheme shows the pendant attachment of ibuprofen and naproxen, one skilled in the art may pendantly attach alternative non-steroidal anti-inflammatory agents as described herein. Similarly, diols other than 1,8-octanediol may also be used to generate "L", for example, such as 1,3-propanediol, and 1,5-pentanediol.
Figure 1:
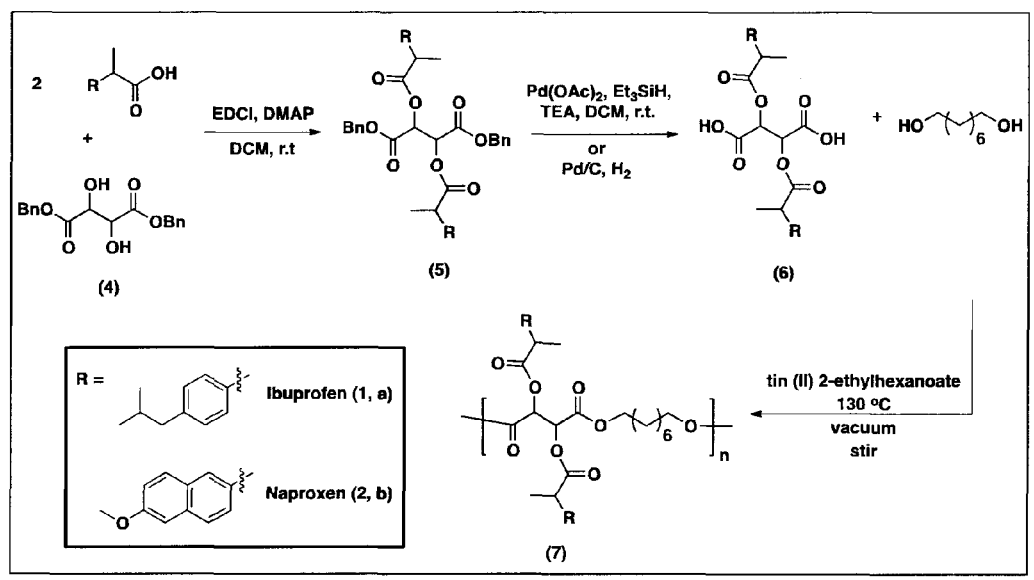

As used herein, a polyester is a polymer that has ester bonds in the backbone of the polymer. In one embodiment the polyester is formed from monomer units that react to provide the ester bonds.

Certain embodiments of the invention provide a polyester comprising one or more groups of formula (I):

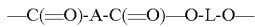
(I)

wherein A is a $C_1$-$C_8$ methylene chain that is covalently linked to one or more residues of a non-steroidal anti-inflammatory; and L is a $C_2$-$C_{10}$ branched or straight chain alkyl or is a residue of formula (III):

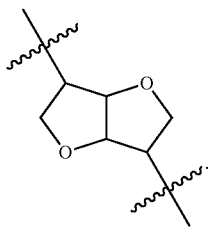
(III)

Certain embodiments of the invention provide a polyester comprising one or more groups of formula (I):

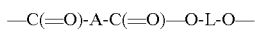
(I)

wherein A is a $C_1$-$C_8$ methylene chain that is covalently linked to one or more residues of a non-steroidal anti-inflammatory; and L is a $C_2$-$C_{10}$ branched or straight chain alkyl.

Certain embodiments of the invention provide a polyester comprising one or more groups of formula (I):

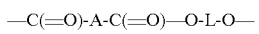
(I)

wherein A is a $C_1$-$C_8$ methylene chain that is covalently linked to one or more residues of a non-steroidal anti-inflammatory; and L is a residue of formula (III):

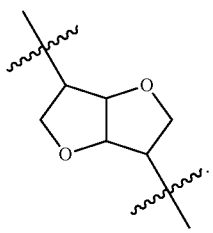
(III)

In certain embodiments, the $C_1$-$C_8$ methylene chain is covalently linked to the one or more residues of the non-steroidal anti-inflammatory through an amine, ester, amide, sulfide, or ether linkage.

In certain embodiments, the $C_1$-$C_8$ methylene chain is covalently linked to the one or more residues of the non-steroidal anti-inflammatory through an ester, thioester, amide, thioamide, urethane, carbamate or carbonate linkage.

In certain embodiments, A is a $C_1$-$C_4$ methylene chain.

In certain embodiments, a polyester as described herein comprises one or more groups of formula (Ia):

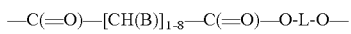
(Ia)

wherein each B is independently a residue of a non-steroidal anti-inflammatory.

In certain embodiments, a polyester as described herein comprises one or more groups of formula (Ia):

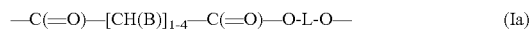
(Ia)

wherein each B is independently a residue of a non-steroidal anti-inflammatory.

In certain embodiments, a polyester as described herein comprises one or more groups of formula (II):

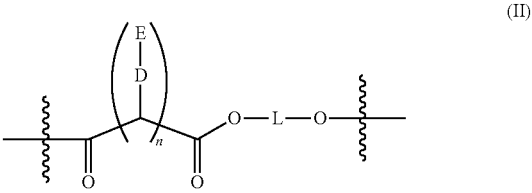
(II)

wherein each D is independently a direct bond, or an ester, thioester, amide, thioamide, urethane, carbamate or carbonate linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl or is a residue of formula (III):

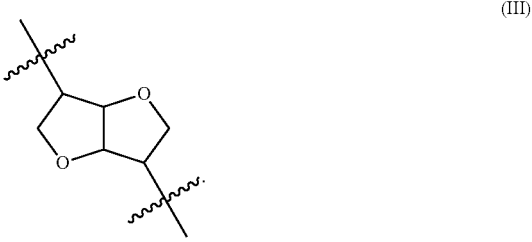 [SMILES: *C1COC2C(*)COC12]
(III)

In certain embodiments, a polyester as described herein comprises one or more groups of formula (II):

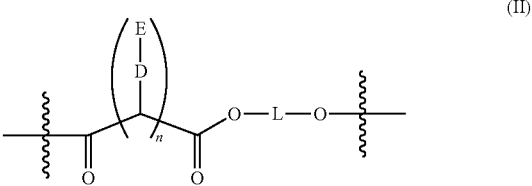
(II)

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl or is a residue of formula (III):

(III)

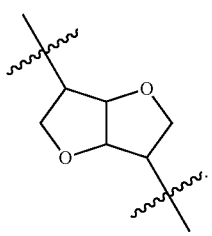

In certain embodiments, a polyester as described herein comprises one or more groups of formula (II):

(II)

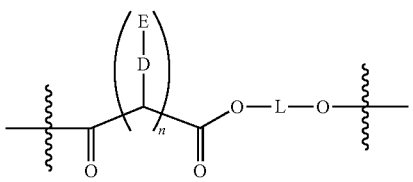

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl.

In certain embodiments, a polyester as described herein comprises one or more groups of formula (II):

(II)

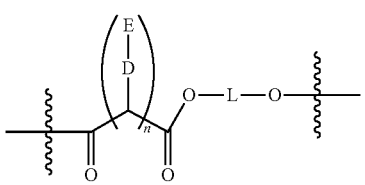

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a residue of formula (III):

(III)

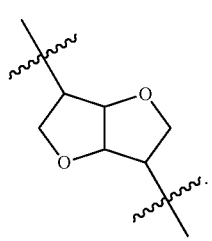

In certain embodiments, n is 1. In certain embodiments, n is 2. In certain embodiments, n is 3. In certain embodiments, n is 4.

In certain embodiments, D is a direct bond, or an ester or amide linkage.

In certain embodiments, D is —O—.

In certain embodiments, a polyester as described herein comprises one or more groups of formula (IIa):

(IIa)

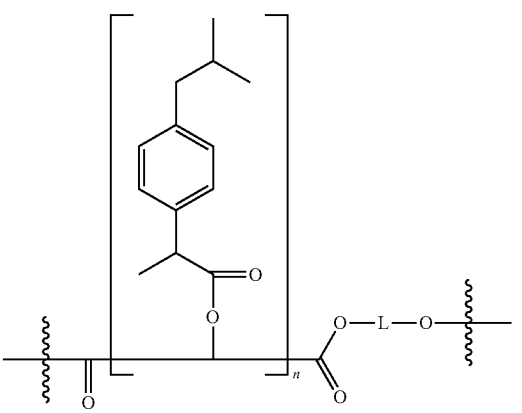

wherein n is 1, 2, 3, 4, 5, 6, 7, 8, or 9; and
wherein L is a $C_2$-$C_{10}$ branched or straight chain alkyl.

In certain embodiments, n is 1. In certain embodiments, n is 2. In certain embodiments, n is 3. In certain embodiments, n is 4.

In certain embodiments, a polyester as described herein comprises one or more groups of formula (IIa):

(IIa)

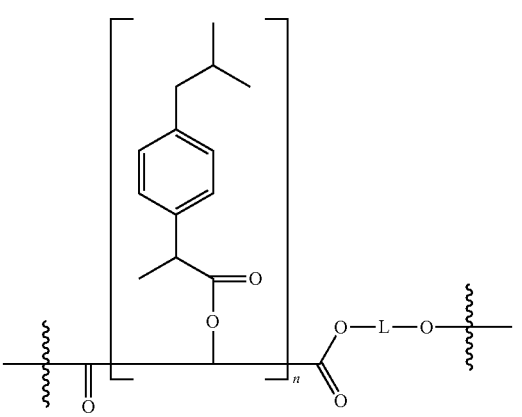

wherein n is 1, 2, 3, 4, 5, 6, 7, 8, or 9; and
wherein L is a residue of formula (III):

(III)

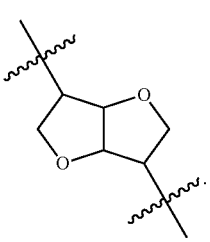

In certain embodiments, n is 1. In certain embodiments, n is 2. In certain embodiments, n is 3. In certain embodiments, n is 4.

In certain embodiments, a polyester as described herein comprises one or more groups of formula (IIb):

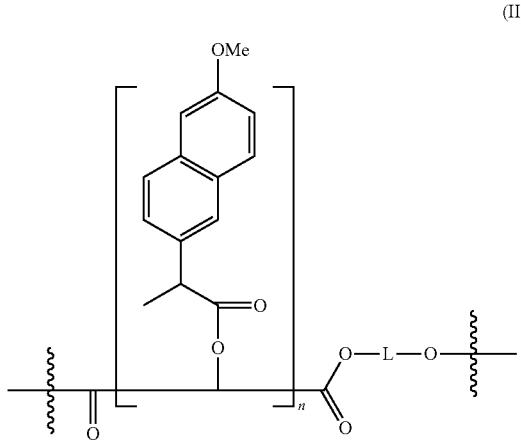
(IIb)

wherein n is 1, 2, 3, 4, 5, 6, 7, 8, or 9; and
wherein L is a $C_2$-$C_{10}$ branched or straight chain alkyl.

In certain embodiments, n is 1. In certain embodiments, n is 2. In certain embodiments, n is 3. In certain embodiments, n is 4.

In certain embodiments, a polyester as described herein comprises one or more groups of formula (IIb):

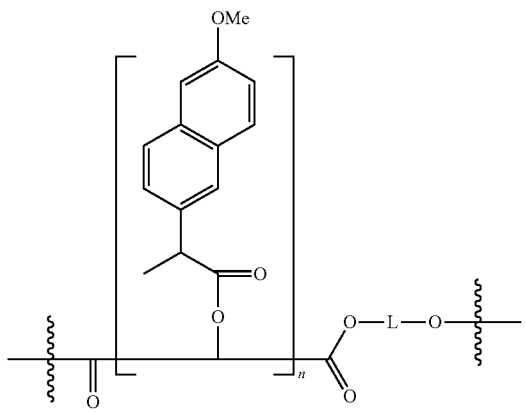
(IIb)

wherein n is 1, 2, 3, 4, 5, 6, 7, 8, or 9; and
wherein L is a residue of formula (III):

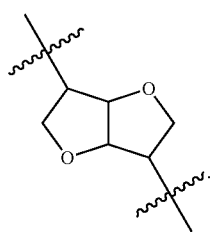
(III)

In certain embodiments, n is 1. In certain embodiments, n is 2. In certain embodiments, n is 3. In certain embodiments, n is 4.

In certain embodiments, a polyester as described herein comprises two or more repeating groups of formula (II):

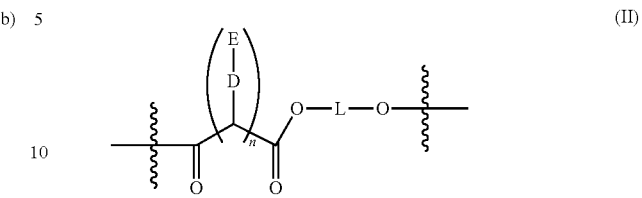
(II)

wherein each D is independently a direct bond, or an ester, thioester, amide, thioamide, urethane, carbamate or carbonate linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl or is a residue of formula (III):

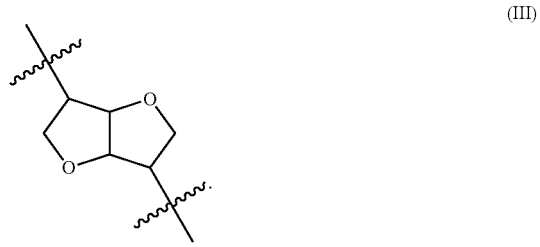 [SMILES: *C1COC2C(*)COC12]
(III)

In certain embodiments, a polyester as described herein comprises two or more repeating groups of formula (II):

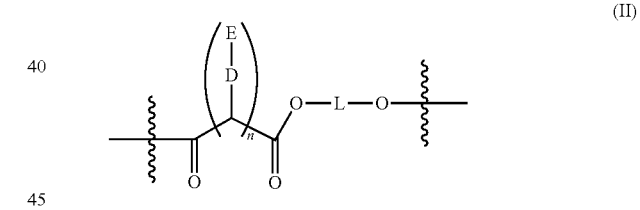
(II)

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl or is a residue of formula (III):

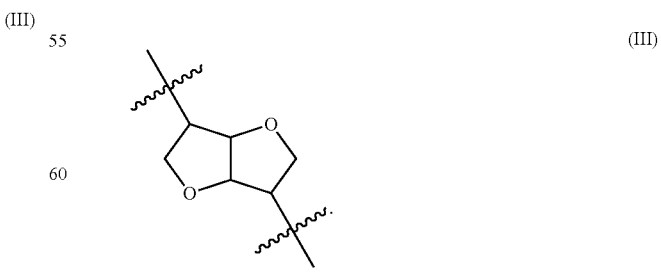
(III)

In certain embodiments, a polyester as described herein comprises two or more repeating groups of formula (II):

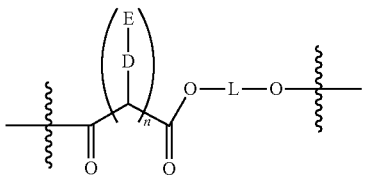

(II)

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a $C_2$-$C_{10}$ branched or straight chain alkyl.

In certain embodiments, a polyester as described herein comprises two or more repeating groups of formula (II):

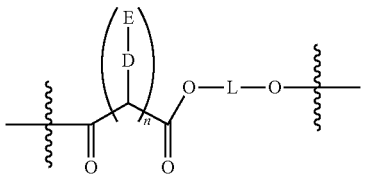

(II)

wherein each D is independently a direct bond, or an amine, ester, amide, sulfide, or ether linkage; each E is independently a residue that will release a non-steroidal anti-inflammatory agent upon hydrolysis of the polymer; n is 1, 2, 3, 4, 5, 6, 7, 8, or 9; and L is a residue of formula (III):

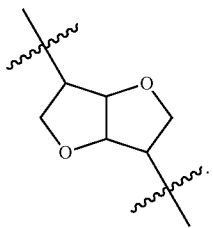

(III)

In certain embodiments, n is 1. In certain embodiments, n is 2. In certain embodiments, n is 3. In certain embodiments, n is 4.

In certain embodiments, D is a direct bond, or an ester or amide linkage.

In certain embodiments, D is —O—.

In certain embodiments, a polyester as described herein comprises 2-200 repeating groups of formula (II). In certain embodiments, a polyester as described herein comprises about 2-150 repeating groups of formula (II). In certain embodiments, a polyester as described herein comprises about 2-100 repeating groups of formula (II). In certain embodiments, a polyester as described herein comprises about 2-75 repeating groups of formula (II). In certain embodiments, a polyester as described herein comprises about 5-50 repeating groups of formula (II). In certain embodiments, a polyester as described herein comprises about 5-25 repeating groups of formula (II).

In certain embodiments, a polyester as described herein comprises at least 2, 3, 4, 5, 6, 7, 8, 9, 10, 11, 12, 13, 14, 15, 16, 17, 18, 19, 20, 21, 22, 23, 24 or 25 repeating groups of formula (II).

In certain embodiments, a polyester as described herein comprises at least 2, 3, 4, 5, 6, 7, 8, or 9 repeating groups of formula (II).

In certain embodiments, a polyester as described herein comprises two or more repeating groups of formula (IIa):

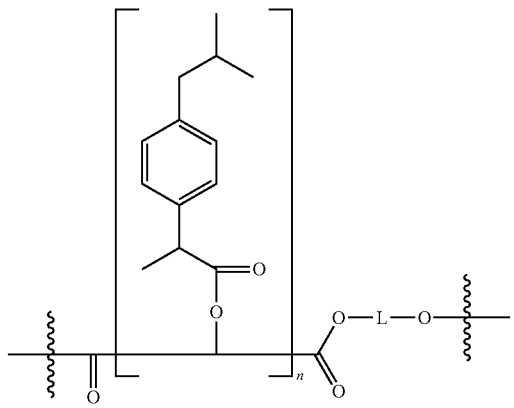

(IIa)

wherein n is 1, 2, 3, 4, 5, 6, 7, 8, or 9; and
wherein L is a $C_2$-$C_{10}$ branched or straight chain alkyl.

In certain embodiments, n is 1. In certain embodiments, n is 2. In certain embodiments, n is 3. In certain embodiments, n is 4.

In certain embodiments, a polyester as described herein comprises two or more repeating groups of formula (IIa):

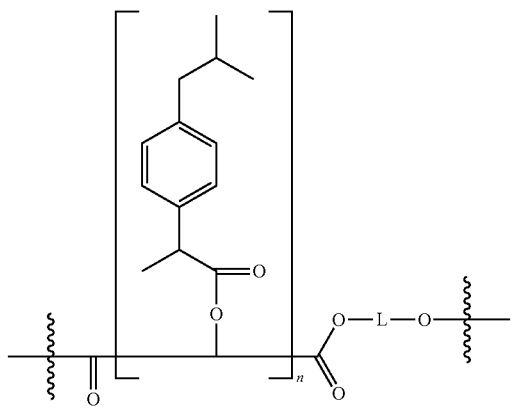

(IIa)

wherein n is 1, 2, 3, 4, 5, 6, 7, 8, or 9; and
wherein L is a residue of formula (III):

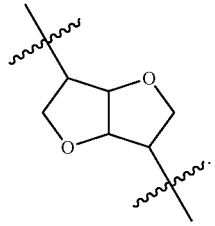

(III)

In certain embodiments, n is 1. In certain embodiments, n is 2. In certain embodiments, n is 3. In certain embodiments, n is 4.

In certain embodiments, a polyester as described herein comprises two or more repeating groups of formula (IIb):

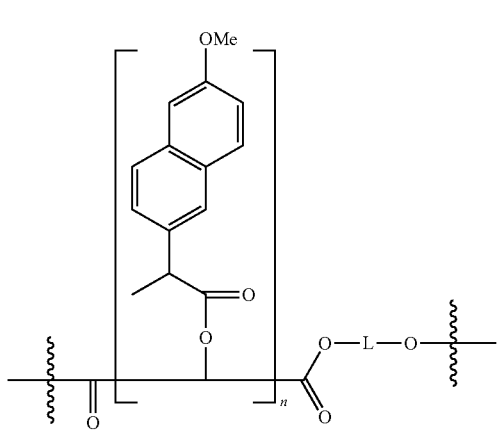

(IIb)

wherein n is 1, 2, 3, 4, 5, 6, 7, 8, or 9; and
wherein L is a $C_2$-$C_{10}$ branched or straight chain alkyl.

In certain embodiments, n is 1. In certain embodiments, n is 2. In certain embodiments, n is 3. In certain embodiments, n is 4.

In certain embodiments, a polyester as described herein comprises two or more repeating groups of formula (IIb):

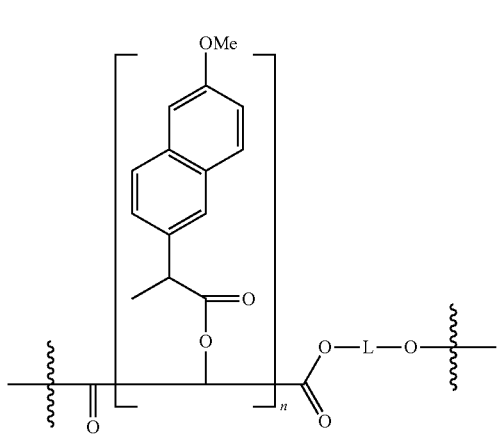

(IIb)

wherein n is 1, 2, 3, 4, 5, 6, 7, 8, or 9; and
wherein L is a residue of formula (III):

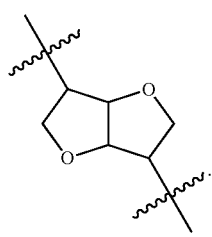

(III)

In certain embodiments, n is 1. In certain embodiments, n is 2. In certain embodiments, n is 3. In certain embodiments, n is 4.

In certain embodiments, a polyester as described herein comprises 2-200 repeating groups of formula (IIa) or (IIb). In certain embodiments, a polyester as described herein comprises about 2-150 repeating groups of formula (IIa) or (IIb). In certain embodiments, a polyester as described herein comprises about 2-100 repeating groups of formula (IIa) or (IIb). In certain embodiments, a polyester as described herein comprises about 2-75 repeating groups of formula (IIa) or (IIb). In certain embodiments, a polyester as described herein comprises about 5-50 repeating groups of formula (IIa) or (IIb). In certain embodiments, a polyester as described herein comprises about 5-25 repeating groups of formula (IIa) or (IIb).

In certain embodiments, a polyester as described herein comprises at least 2, 3, 4, 5, 6, 7, 8, 9, 10, 11, 12, 13, 14, 15, 16, 17, 18, 19, 20, 21, 22, 23, 24 or 25 repeating groups of formula (IIa) or (IIb).

In certain embodiments, a polyester as described herein comprises at least 2, 3, 4, 5, 6, 7, 8, or 9 repeating groups of formula (IIa) or (IIb).

Non-steroidal anti-inflammatory agents (NSAIDs) are a well-known class of drugs that includes, for example, ibuprofen, naproxen, fenoprofen, ketoprofen, flurbiprofen, suprofen, benoxaprofen, indoprofen, pirprofen, carprofen, loxoprofen, pranoprofen, alminoprofen, salicylic acid, diflunisal, salsalate, oxaprozin, indomethacin, sulindac, etodolac, ketorolac, diclofenac, piroxicam, meloxicam, tenoxican, lomoxicam, isoxicam, mefenamic acid, meclofenamic acid, flufenamic acid, tolfenamic acid, lumiracoxib and licofelone.

Accordingly, in certain embodiments, each non-steroidal anti-inflammatory agent is selected from ibuprofen, naproxen, fenoprofen, ketoprofen, flurbiprofen, suprofen, benoxaprofen, indoprofen, pirprofen, carprofen, loxoprofen, pranoprofen, alminoprofen, salicylic acid, diflunisal, salsalate, oxaprozin, indomethacin, sulindac, etodolac, ketorolac, diclofenac, piroxicam, meloxicam, tenoxican, lomoxicam, isoxicam, mefenamic acid, meclofenamic acid, flufenamic acid, tolfenamic acid, lumiracoxib and licofelone.

In certain embodiments the NSAID is ibuprofen.
In certain embodiments the NSAID is naproxen.

NSAIDs may be incorporated into the polymers of the invention as pendant groups that are not part of the backbone of the polymer. As such, a tracing of the chain of atoms that form the backbone of the polymer would not include the atoms of the residues of the NSAIDs. In certain embodiments of the invention, the pendant groups can be considered to be sidechains of the polymer. In certain embodiment, NSAIDs can be attached to the remainder of the polymer of the invention through labile (e.g., anhydride, ester, amide or thioester linkages) bonds, that allow for release of the NSAIDs upon degradation (e.g., hydrolysis). In certain embodiment, NSAIDs can be attached to the remainder of the polymer of the invention through labile (e.g., ester, thioester, amide, thioamide, urethane, carbamate or carbonate linkages) bonds, that allow for release of the NSAIDs upon degradation (e.g., hydrolysis).

In certain embodiments, L is a $C_2$-$C_{10}$ straight chain alkyl.
In certain embodiments, L is a $C_4$-$C_8$ straight chain alkyl.
In certain embodiments, L is a $C_2$, $C_3$, $C_4$, $C_5$, $C_6$, $C_7$, $C_6$, $C_8$, $C_9$ or $C_{10}$ straight chain alkyl.
In certain embodiments, L is a $C_6$ straight chain alkyl.
In certain embodiments, L is a $C_2$-$C_{10}$ branched chain alkyl.
In certain embodiments, L is a $C_4$-$C_8$ branched chain alkyl.
In certain embodiments, L is a $C_2$, $C_3$, $C_4$, $C_5$, $C_6$, $C_7$, $C_6$, $C_8$, $C_9$ or $C_{10}$ branched chain alkyl.
In certain embodiments, L is a $C_6$ branched chain alkyl.

In certain embodiments, the residue of formula (III) is a residue of formula (IIIa)

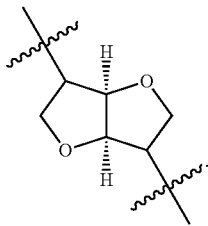

(IIIa)

In certain embodiments, the residue of formula (III) is a residue of formula (IIIb):

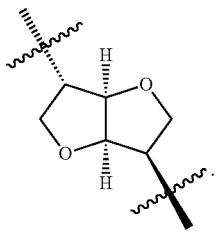

(IIIb)

In certain embodiments, the formula IIb is a formula of IIb':

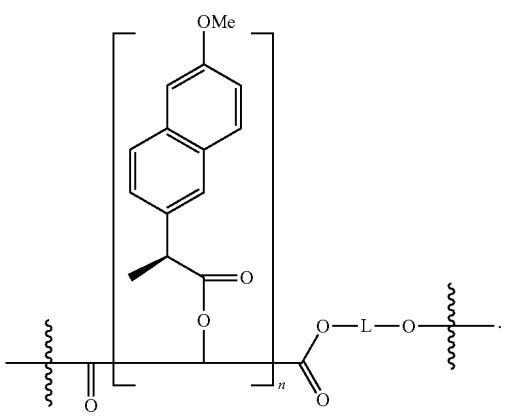

(IIb')

In certain embodiments, a polyester as described herein and prepared in accordance with the present invention has an average molecular weight of about 1,000 daltons to about 100,000 daltons. In certain embodiments, the polymer has an average molecular weight of about 4,000 daltons to about 100,000 daltons. In certain embodiments, the polymer has an average molecular weight of about 4,000 daltons to about 50,000 daltons. In certain embodiments, the polymer has an average molecular weight of about 4,000 daltons to about 30,000 daltons. In certain embodiments, the polymer has an average molecular weight of about 4,000 daltons to about 20,000 daltons. In certain embodiments, the polymer has an average molecular weight of about 4,000 daltons to about 16,000 daltons.

Certain embodiments of the invention provide a pharmaceutical composition comprising a polyester as described herein and a pharmaceutically acceptable carrier.

Certain embodiments of the invention provide a method to treat pain or inflammation in a mammal (e.g., a human), comprising administering a polyester as described herein to the mammal.

Certain embodiments of the invention provide a method to treat an inflammatory disease in a mammal (e.g., human), comprising administering a polyester as described herein to the mammal.

As used herein, the terms "treat" and "treatment" can refer to therapeutic treatment or to prophylactic or preventative treatment, wherein the object is to prevent or decrease an undesired physiological change or disorder, such as disorders associated with pain or inflammation.

Administration

The polyesters described herein can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present polyesters may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the present polyesters may be combined with one or more excipients and used in the form of ingestible tablets, buccal tablets, troches, capsules, elixirs, suspensions, syrups, wafers, and the like. Such compositions and preparations should contain at least 0.1% of active compound. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a poly(ethylene glycol). Various other materials may be present as coatings or to otherwise modify the physical form of the solid unit dosage form. For instance, tablets, pills, or capsules may be coated with gelatin, wax, shellac or sugar and the like. A syrup or elixir may contain the present polyesters, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the present polyesters may be incorporated into sustained-release preparations and devices.

The present polyesters may also be administered intravenously or intraperitoneally by infusion or injection. Solutions of the present polyesters can be prepared in water, optionally mixed with a nontoxic surfactant. Dispersions can also be prepared in glycerol, liquid poly(ethylene glycols), triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the present polyesters which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid poly(ethylene glycols), and the like), vegetable oils, nontoxic glyceryl esters, and suitable mixtures thereof. The proper fluidity can be maintained by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the present polyesters in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the present polyesters plus any additional desired ingredient present in the previously sterile-filtered solutions.

For topical administration, the present polyesters may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present polyesters to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the present polyesters can be determined by comparing their in vitro activity, and in vivo activity in animal models. Methods for the extrapolation of effective dosages in mice, and other animals, to humans are known to the art; for example, see U.S. Pat. No. 4,938,949.

The amount of the present polyesters, or derivative thereof, required for use in treatment will vary with the route of administration, the nature of the condition being treated and the age and condition of the patient and will be ultimately at the discretion of the attendant physician or clinician.

The present polyesters may conveniently be formulated in unit dosage form. In one embodiment, the invention provides a composition comprising a polyester of the invention formulated in such a unit dosage form.

Compounds of the invention can also be administered in combination with other therapeutic agents, for example, other agents that are useful for the treatment of pain or inflammation in a mammal (e.g., a human). Examples of such agents include, but are not limited to, analgesics and anti-inflammatory agents, such as NSAIDs and opioids or any therapeutic that would be used to reduce pain and/or inflammation. In certain embodiments, the agent may be insulin, which could further mediate inflammation in a diabetic patient. In certain embodiments, the agent may be a growth factor or a protein/peptide. In certain embodiments, the peptide may be Glucagon-like Peptide 1 or C-peptide, which could further mediate inflammation in a diabetic patient.

Specific examples of such other therapeutic agents include, but are not limited to, paracetamol, parecoxib, nefopam, pethidine, ketamine, lidocaine, dilofenac, rofecoxib, celecoxib, etoricoxib, venlafaxine, imipramine, duloxetine, bupropion, gabapentin, pregabalin, lamotrigine, diamorphine, 3-amino-4-hydroxybutyric acid, aceclofenac, bromfenac, bumadizon, enfenamic acid, fendosal, gentisic acid, mesalamine, niflumic acid, olsalazine, oxaceprol, S-adenosylmethionine, sulfasalazine, ibuprofen, naproxen, fenoprofen, ketoprofen, flurbiprofen, suprofen, benoxaprofen, indoprofen, pirprofen, carprofen, loxoprofen, pranoprofen, alminoprofen, salicylic acid, diflunisal, salsalate, oxaprozin, indomethacin, sulindac, etodolac, ketorolac, diclofenac, piroxicam, meloxicam, tenoxican, lornoxicam, isoxicam, mefenamic acid, meclofenamic acid, flufenamic acid, tolfenamic acid, lumiracoxib, licofelone, A-methylfentanyl, Alfentanil, Allylprodine, Bezitramide, Buprenorphine, Butorphanol, Carfentanyl, Desmethylprodine, Dextromoramide, Dezocine, Diacetylmorphine, Dihydrocodeinone, Dihydroetorphine, Dimorphone, Diphenoxylate, Dipipanone, Etorphine, Fentanyl, Ketobemidone, Lefetamine, Levacetylmethadol, Levomethorphan, Levorphanol, Loperamide, Meperidine, Meptazinol, Methadone, Methylmorphine, Morphine, Nalbuphine, Nalmefene, Naloxone, Naltrexone, Nicomorphine, Ohmefentanyl, Oripavine, Oxycodone, Oxymorphone, PEPAP, Papaver somniferum, Paramorphine, Pentazocine, Phenazocine, Piritramide, Prodine, Remifentanil, Sufentanil, Tapentadol, Tilidine, Tramadol, insulin, Glucagon-like Peptide 1, C-peptide, N-terminal peptide of annexin A1 (peptide Ac2-26), infliximab, anti-CD11b/CD18 antibodies, anti-TNF-alpha monoclonal antibody, agents listed in *Drugs,* 67(15), 2121-2133 (2007), and the like.

Accordingly, one embodiment the invention also provides a composition comprising a polyester described herein, at least one other therapeutic agent (e.g., admixed in the polymer matrix), and a pharmaceutically acceptable diluent or carrier. The invention also provides a kit comprising a polyester described herein, at least one other therapeutic agent, packaging material, and instructions for administering the polyester and the other therapeutic agent or agents to a mammal (e.g., human) to treat pain or inflammation.

The following non-limiting examples set forth herein below illustrate certain aspects of the invention.

EXAMPLES

The polymers described herein are advantageous over existing systems as they exhibit higher drug loadings (i.e., approximately 65-75%), are biodegradable, and have a more controlled and tuneable release profile that can be potentially adjusted for different in vivo applications. These polymers will provide a greater range of release rates and formulation possibilities than the typical free-drug forms of the NSAIDs. Unlike the free-drug forms, these polymers can be fabricated into various geometries with different physical and mechanical properties. These polymers may be used to make implantable and injectable delivery systems that would be ideal for providing sustained and localized inflammation treatment while decreasing the common side effects associated with oral delivery of propionic acid-derived NSAIDs.

Example 1

Biodegradable Polyesters Containing Ibuprofen and Naproxen as Pendant Groups

SUMMARY

Controlled release of non-steroidal anti-inflammatory drugs such as ibuprofen and naproxen could be beneficial for the treatment of inflammatory diseases while reducing the side effects resulting from their continuous use. Novel biodegradable polyesters solely comprised of biocompatible components (e.g., tartaric acid, 1,8-octanediol, and ibuprofen or naproxen as pendant groups) have been synthesized using tin (II) 2-ethylhexanoate as catalyst at 130° C. and subsequently characterized by nuclear magnetic resonance and infrared spectroscopies. In addition, the weight-average molecular weight and thermal properties were determined. The polymers release the free drug (ibuprofen or naproxen) in vitro in a controlled manner without burst release. These new biomaterials are not cytotoxic towards mouse fibroblasts up to 0.10 mg/mL and the drugs retain their chemical structure following hydrolytic degradation of the polymer.

Introduction

Non-steroidal anti-inflammatory drugs (NSAIDs) have analgesic, antipyretic, and anti-inflammatory activity. Ibuprofen (1) and naproxen (2), FIG. 1, are propionic acid-derivative NSAIDs commonly used to treat pain and swelling associated with rheumatoid arthritis, osteoarthritis, psoriatic arthritis, and Ankylosing spondylitis. Administration of high systemic doses is often required to treat these chronic conditions because both 1 and 2 have relatively short half-life in plasma (2.1 and 14 hours, respectively). When repeatedly administered, severe gastrointestinal side effects such as stomach ulceration, bleeding, and perforation occur because the drug is distributed throughout the body to targeted and non-targeted sites. Therefore, the therapeutic potentials of 1 and 2 could be significantly enhanced by incorporating them into controlled-delivery systems.

Drug delivery systems have been developed to localize drug release and prolong the duration of drug effect. The preparation of polymer microparticles encapsulating 1 or 2 has been studied (Arica, et al., *J. Microencapsulation* 2005, 22, 153-165; Thompson, et al., *J. Microencapsulation* 2009, 26 (8), 676-683; Fernández-Carballido, et al., *Int. J. Pharm.* 2004, 279, 33-41; Bozdag, et al., *J. Microencapsulation* 2001, 18, 443; Castelli, et al., *Int. J. Pharm.* 1998, 176, 85-98; Borovac, et al., *J. Controlled Release* 2006, 115, 266-274; Thompson, et al., *Int. J. Pharm.* 2007, 329, 53-61). The major issues associated with this type of drug delivery system are low drug loading (less than 30%), burst release and short-term (rapid) drug release. Acrylic and vinyl polymers have been widely studied to conjugate 1 or 2 onto the polymer backbones (Khan, et al., *Eur. J. Med. Chem.* 2005, 40, 371-376; Mirzaagha, B., *Int. J. Pharm.* 2008, 356, 167-173; Gallardo, et al., *J. Controlled Release* 2001, 71, 127-140; Mizrahi, et al., *AAPS PharmSciTech* 2009, 10, 453-458; Liso, et al., *J. Controlled Release* 1995, 33, 429-436; Babazadeh, M., *Int. J. Pharm.* 2006, 316, 68-73; Davaran, S.; Entezami, A., A., *Anglais* 1998, 34, 187-192). Although these polymers are biocompatible, they are not biodegradable (Pillai, et al., *Curr. Opin. Chem. Biol.* 2001, 5, 447-451). Therefore, when the entire drug is released, the polymer would remain in the body which could cause patient discomfort and adverse effects (Jain, J. P.; Modi, S.; Domb, A. J.; Kumar, N., *J. Controlled Release* 2005, 103, 541-563). Despite the limitations, these drug delivery systems have been shown to lower the side effects associated with the systemic administration of the drug and to increase the duration of the drugs' anti-inflammatory effects. To overcome these issues, chemical incorporation of bioactive molecules into biodegradable polymer backbones as a unique drug delivery method was proposed. Drugs containing only one reactive functional group can be incorporated onto a polymer as pendant groups; this type of chemical incorporation with phenolic antiseptics was explored, achieving high drug loading (48-58 wt. %) (Prudencio, et al., *Macromol. Rapid Commun.* 2009, 30, 1101-1108).

In this work, bioactives 1 and 2 were incorporated into biodegradable polyester backbones through their propionic acid moiety. Thus, polymers containing 65-67 wt. % of drug into the polymer that upon hydrolytic degradation, releases bioactives 1 and 2 in a controlled manner, were designed. This work presents the synthesis and characterization of biodegradable ibuprofen- and naproxen-based polyesters. Tartaric acid (e.g., L-tartaric acid, D-tartaric acid, DL-tartaric acid) (FIG. 1, 3), a naturally occurring and biocompatible compound that has antioxidant properties (DeBolt, S.; Cook, D. R.; Ford, C. M., *Proc. Natl. Acad. Sci.* 2006, 103, 5608-5613), was used as the polymer backbone. The polymers were synthesized at 130° C. catalyzed by tin (II) 2-ethylhexanoate. Chemical structures and physical properties of all compounds were measured, and in vitro release studies performed in phosphate buffered saline (PBS) at 37° C. to mimic physiological conditions. The cytocompatibilities of the polymers towards mouse fibroblasts at various concentrations were determined. Lastly, the structural integrities of the released drugs were studied.

Experimental Section

Materials.

Naproxen and 1-[3-(dimethylamino)propyl]-3-ethylcarbodiimide hydrochloride (EDCI) were purchased from Fisher Scientific (Pittsburg, Pa.). NCTC clone 929 (strain L) mouse areolar fibroblast cells were purchased from ATCC (Manassas, Va.). Fetal bovine serum (FBS), penicillin/streptomycin (pen/strep), L-Glutamine, trypsin-ethylenediaminetetraacetic acid (trypsin-EDTA), and Dulbecco's modified eagle medium (DMEM) were obtained from GIBCO BRL (Rockville, Md.). CellTiter 96® Aqueous One Solution Cell Proliferation Assay was obtained from Promega (Madison, Wis.). All other chemicals and reagents were purchased from Sigma-Aldrich (Milwaukee, Wis.) and used as received.

Proton and Carbon Nuclear Magnetic Resonance ($^1$H- and $^{13}$C-NMR) Spectroscopies.

$^1$H- and $^{13}$C-NMR spectra were obtained using a Varian 500 MHz spectrometer. Samples were dissolved (~5 mg/mL for $^1$H-NMR and ~20 mg/mL for $^{13}$C-NMR) in deuterated chloroform (CDCl$_3$), with trimethylsilane as internal reference. Each spectrum was an average of 16 and 250 scans, respectively.

Infrared (IR) Spectroscopies.

Fourier transform IR (FT-IR) spectra were obtained using a Thermo Nicolet/Avatar 360 FT-IR spectrometer. Samples (1 wt. %) were solvent-cast onto NaCl plates using dichloromethane (DCM). Each spectrum was an average of 32 scans.

Molecular Weight.

Mass spectrometry (MS) was used to determine the molecular weights (MW) of polymer intermediates. A Finnigan LCQ-DUO equipped with Xcalibur software and an adjustable Atmospheric Pressure ionization Electrospray Ion Source (API-ESI) were used. Samples were dissolved in methanol (MeOH) and diluted to 10 μg/mL before injection using a glass syringe. Pressure during the experiments was $0.8 \times 10^{-5}$ Torr and the API temperature was 150° C.

Gel permeation chromatography (GPC) was used to determine weight-average molecular weight ($M_w$) and polydispersity index (PDI) of the polymers. Waters system consisting of a 515 HPLC pump, a 717 plus autosampler, and a 410 refractive index (RI) detector was used. Waters Empower 2 software was used for data collection and analysis. Samples were dissolved in tetrahydrofuran (10 mg/mL), 20 μL aliquot was injected, and eluted through two PL gel columns $10^3$ and $10^5$ Å (Polymer Laboratories) used in series at a flow rate of 1 mL/min. The $M_w$ was calculated relative to narrow $M_w$ polystyrene standards.

Thermal Analysis.

TGA was used to obtain the decomposition temperatures ($T_d$). TGA analysis was performed using a Perkin-Elmer TGA7 analyzer with TAC7/DX controller equipped with a Dell OptiPlex Gx 110 computer running Perkin-Elmer Pyris software. Samples (~10 mg) were heated under nitrogen at a rate of 10° C./min from 25 to 400° C. $T_d$ was defined as the onset of decomposition and represented by the beginning of a sharp slope on the thermogram.

Thermal analysis was performed using DSC to obtain the glass transition ($T_g$) and melting ($T_m$) temperatures. DSC was performed using a Thermal Advantage (TA) DSC Q200 running on an IBM ThinkCentre computer equipped with TA Instrument Explorer software for data collection and control. Samples (4-8 mg) were heated under nitrogen from −40° C. to 200° C. at a heating rate of 10° C./min. Two heating/cooling cycles were used for each sample set. TA Universal Analysis 2000, version 4.5A was used to analyze the data. $T_g$ was defined as the midpoint of the curve and $T_m$ as the peak maximum.

Ibuprofen-tartrate Protected Diacid Synthesis (5a in FIG. 1B).

Ibuprofen (1, 3.21 g, 2.2 eq) was dissolved in anhydrous DCM and stirred under argon. Then 4-(dimethylamino)pyridine (DMAP, 1.9 g, 2.2 eq) was added to the reaction mixture. Dibenzyl-L-tartrate (4, 2.34 g, 1 eq) was dissolved in anhydrous DCM and added to the reaction mixture followed by the addition of EDCI (6.0 g, 4.4 eq). The resulting yellowish solution was stirred for 2 h. The reaction mixture was diluted with ethyl acetate (EtOAc), extracted with 10% $KHSO_4$ and saturated $NaHCO_3$. The organic layer was dried over $MgSO_4$ and the solvent evaporated under reduced pressure to give a brown, viscous oil that was dried in vacuo at room temperature overnight. Yield: 93%. $^1$H-NMR (CDCl$_3$, 500 MHz, δ): 7.30 (6H, m, ArH), 7.16 (6H, m, ArH), 7.06 (6H, m, ArH), 5.67 (2H, split, CH), 5.05-4.53 (4H, split, CH2), 3.80-3.60 (2H, dm, CH), 2.41 (4H, m, CH$_2$), 1.79 (2H, m, CH), 1.45 (6H, t, CH$_3$), 0.86 (12H, d, CH$_3$). $^{13}$C-NMR (CDCl$_3$, 500 MHz, δ): 173.5 (1C), 173.2 (1C), 165.7 (1C), 165.3 (1C), 140.9 (2C), 136.9 (2C), 135.0 (2C), 129.5 (6C), 128.6 (6C), 127.7 (6C), 71.1 (2C), 67.7 (2C), 45.1 (2C), 44.7 (2C), 30.4 (2C), 22.7 (4C), 18.5 (2C). IR: 1769 cm$^{-1}$ (C=O ester) and 1751 cm$^{-1}$ (C=O ester). MS: M/Z=729 [M+Na]. $T_d$=237° C.

Naproxen-Tartrate Protected Diacid Synthesis (5b in FIG. 1B).

Synthesis of 5b was performed using the procedure described for 5a in Section 2.5.1 using 2.2 eq of naproxen (2) instead of 1. Yield: 81% (green foam). $^1$H-NMR (CDCl$_3$, 500 MHz, δ): 7.64 (6H, t, ArH), 7.37 (2H, d, ArH), 7.18 (6H, m, ArH), 7.10 (2H, d, ArH), 7.03 (2H, d, ArH), 6.83 (4H, d, ArH), 5.62 (2H, s, CH), 4.57-4.29 (4H, dd, CH$_2$), 3.93 (2H, m, CH), 3.88 (6H, s, OCH$_3$), 1.52 (6H, d, CH$_3$). $^{13}$C-NMR (CDCl$_3$, 500 MHz, δ): 173.5 (2C), 165.4 (2C), 158.0 (2C), 135.1 (2C), 134.6 (2C), 134.0 (2C), 129.6 (2C), 129.1 (2C), 128.6 (4C), 128.5 (2C), 128.0 (6C), 127.4 (2C), 126.5 (2C), 119.3 (2C), 105.8 (2C), 71.2 (2C), 67.6 (2C), 55.5 (2C), 45.0 (2C), 18.4 (2C). IR: 1767 cm$^{-1}$ (C=O ester) and 1748 cm$^{-1}$ (C=O ester). MS: M/Z=777 [M+Na]. $T_d$=294° C.

Ibuprofen-Tartaric Diacid Synthesis (6a in FIG. 1B).

Anhydrous DCM and triethylamine (TEA, 3.0 mL, 2.5 eq) were added to palladium (II) acetate [Pd(OAc)$_2$, 4.23 g, 2.5 eq] and the mixture stirred under argon. Ibuprofen-tartrate protected diacid (5a, 6.00 g, 1 eq) was dissolved in DCM and added dropwise to the reaction mixture. The solution was left stirring for 5 min and triethylsilane (Et$_3$SiH, 34 mL, 25 eq) added dropwise via a syringe pump (over 1 h). The reaction was stirred at room temperature under argon overnight. MeOH (3 mL) was added and the mixture was filtered over celite to remove Pd catalyst. The filtrate was concentrated under reduced pressure and the orange residue diluted in EtOAc. The precipitate formed was removed via vacuum filtration. The filtrate was concentrated under reduced pressure; the orange liquid obtained was diluted in acetonitrile (ACN) and extracted with hexanes. The ACN layer was dried under reduced pressure. The orange residue was diluted in EtOAc and extracted with water. The organic layer was dried over MgSO$_4$ and the solvent evaporated under reduced pressure to give a yellow foam that was dried in vacuo at room temperature overnight. Yield: 77%. $^1$H-NMR (CDCl$_3$, 500 MHz, δ): 7.18 (4H, d, ArH), 7.08 (4H, d, ArH), 5.68 (2H, split, CH), 3.79 (2H, t, CH), 2.5 (4H, m, CH$_2$), 1.84 (2H, m, CH), 1.51 (6H, t, CH$_3$), 0.88 (12H, d, CH$_3$). $^{13}$C-NMR (CDCl$_3$, 500 MHz, δ): 173.6 (1C), 173.3 (1C), 170.7 (1C), 170.2 (1C), 141.0 (2C), 136.7 (2C), 129.5 (4C), 127.6 (4C), 70.5 (2C), 45.1 (2C), 44.8 (2C), 30.4 (2C), 22.6 (4C), 18.4 (2C). IR: 1751 cm$^{-1}$ (C=O ester), 1733 cm$^{-1}$ (C=O acid), and 3231 cm$^{-1}$ (OH acid). MS: M/Z=549 [M+Na]. $T_d$=224° C.

Naproxen-Tartaric Diacid Synthesis (6b in FIG. 1B).

Synthesis was performed using the procedure described for 6a in Section 2.5.1. Yield: 90% (orange foam). $^1$H-NMR (CDCl$_3$, 500 MHz, δ): 7.70 (4H, t, ArH), 7.38 (4H, d, ArH), 7.15 (4H, d, ArH), 5.57 (2H, s, CH), 4.00 (2H, m, CH), 3.91 (6H, s, OCH$_3$), 1.60 (6H, d, CH$_3$). $^{13}$C-NMR (CDCl$_3$, 500 MHz, δ): 173.5 (2C), 160.0 (2C), 157.9 (2C), 135.0 (2C), 134.0 (2C), 129.5 (2C), 127.4 (2C), 126.4 (4C), 126.3 (2C), 119.3 (2C), 105.7 (2C), 71.0 (2C), 55.5 (2C), 44.9 (2C), 18.3 (2C). IR: 1748 cm$^{-1}$ (C=O ester), 1733 cm$^{-1}$ (C=O acid), and 3447 cm$^{-1}$ (OH acid). MS: M/Z=597 [M+Na]. $T_d$=235° C.

Optimized Diacid Synthesis.

Ibuprofen- or naproxen-tartrate protected diacid (5a or 5b, 1 eq) was dissolved in anhydrous DCM (10 mL/g of protected diacid) and 10% palladium on carbon (Pd/C, catalytic amount) was added. The reaction flask was evacuated by vacuum and purged with hydrogen gas (3×). The reaction was stirred at room temperature under hydrogen overnight. The mixture was filtered over celite to remove Pd/C. The filtrate was dried under reduced pressure to give a yellow or orange foam that was dried in vacuo at room temperature overnight. Yield: >90%. The characterization is described in sections 2.5.1 and 2.5.2.

Ibuprofen-Tartaric Polymer Synthesis (7a in FIG. 1B).

Ibuprofen-tartaric diacid (0.51 g, 1 eq), 1,8-octanediol (0.14 g, 1 eq), and tin (II) 2-ethylhexanoate (26.4 μL, 5 wt. %) were added to a double-neck round-bottom flask and degassed through vacuum/argon cycles (3×). The mixture was heated to 130° C. under vacuum (<2 mmHg), and stirred (100 rpm) using an overhead mechanical stirrer (T-line laboratory stirrer, Talboys Engineering Corp., Montrose, Pa.) for 6 h. The product was cooled and dissolved in DCM (minimal amount). The product was isolated by removing the DCM under reduced pressure and dried under vacuum at room temperature overnight. Yield: 0.42 g (82%), orange paste. $^1$H-NMR (CDCl$_3$, 500 MHz, δ): 7.20 (4H, b, ArH), 7.08 (4H, b, ArH), 5.60 (2H, b, CH), 4.10-3.6 (6H, b, CH, CH$_2$), 2.44 (4H, b, CH$_2$), 1.85 (2H, b, CH), 1.60-1.00 (18H, b, CH$_3$, 3CH$_2$), 0.89 (12H, b, CH$_3$). $^{13}$C-NMR (CDCl$_3$, 500 MHz, δ): 173.6 (2C), 165.3 (2C), 140.9 (2C), 136.9 (2C), 129.5 (4C), 127.6 (4C), 71.0 (2C), 66.3 (2C), 45.3 (2C), 44.9 (2C), 30.6 (2C), 29.3 (2C), 28.4 (2C), 25.7 (2C), 22.4 (4C), 18.3 (2C). IR: 1768 and 1750 cm$^{-1}$ (C=O, ester). $M_w$=11,200 Da, PDI=1.4. $T_g$=−17° C. $T_d$=289° C.

Naproxen-Tartaric Polymer Synthesis (7b in FIG. 1B).

Synthesis was performed using the procedure described in Section 2.7.1. Yield: 0.19 g (95%), yellow foam. $^1$H-NMR (CDCl$_3$, 500 MHz, δ): 7.70 (411, b, ArH), 7.39 (411, b, ArH), 7.13 (4H, b, ArH), 5.56 (2H, b, CH), 3.97 (2H, b, CH), 3.91 (6H, b, OCH$_3$), 3.60-3.16 (4H, b, CH$_2$) 1.58 (6H, b, CH$_3$), 1.57-0.64 (12H, b, 3CH$_2$). $^{13}$C-NMR (CDCl$_3$, 500 MHz, δ): 173.5 (2C), 165.6 (2C), 157.9 (2C), 135.0 (2C), 134.0 (2C), 129.6 (2C), 127.4 (2C), 126.4 (4C), 126.3 (2C), 119.3 (2C), 105.7 (2C), 71.2 (2C), 66.2 (2C), 55.4 (2C), 44.9 (2C), 29.1 (2C), 28.1 (2C), 25.4 (2C), 18.3 (2C). IR: 1768 and 1747 cm$^{-1}$ (C=O, ester). $M_w$=6,000 Da, PDI=1.2. $T_g$=23° C. $T_d$=260° C.

In Vitro Drug Release Studies.

Drug (1 and 2) release from their respective polymer (7a and 7b) was studied at 37° C. in PBS (pH 7.4) with agitation (60 rpm) to mimic physiological conditions. Triplicate samples of each polymer (50.0 mg) were placed in 20 mL scintillation vials (Fisher, Fair Lawn, N.J.) with 15 mL of PBS. At predetermined time points, samples were centrifuged at 3,000 rpm for 5 min (Hettich Zentrifugen EBA12) to isolate the polymer. All the degradation media (15 mL) was collected and replaced with fresh PBS (15 mL) at each time point. Samples were immediately analyzed using HPLC as described below.

High-Performance Liquid Chromatography (HPLC).

Quantitative analysis of the in vitro degradation products was performed via HPLC using an XTerra® RP18 5 μm 4.6×150 mm column (Waters, Milford, Mass.) on a Waters 2695 Separations Module equipped with a Waters 2487 Dual λ Absorbance Detector. The system was connected to a Dell computer running Empower software. Samples were filtered using 0.22 μm poly(vinylidine fluoride) syringe filters (Fisher). The HPLC method was adapted from previously published methods (Mizrahi, et al., *AAPS PharmSciTech* 2009, 10, 453-458; Basheer, et al., *Anal. Chem.* 2007, 79, 6845-6850). The mobile phase was 10 mM KH$_2$PO$_4$, 70% ACN, and 30% water at pH 3.5. Samples (20 μL) were run at 25° C. at a flow rate of 1 mL/min. Absorbance was monitored at λ=265 nm for both drugs. The instrument was calibrated using standard 1 and 2 solutions of known concentrations.

Structure Determination of Released Drugs.

Release media from day 5 (time point with the highest drug concentration) were freeze-dried for 24 h at −40° C. and 133×10$^{-3}$ mBar (LABCONO Freeze Dry System/Freezon 4.5). The resulting white powder was dissolved in acidic water (5 mL, pH~1) and extracted with DCM (5×3 mL). DCM was evaporated under reduced pressure and the samples dried under vacuum for 2 days. Solutions of the free drugs (1 and 2) were prepared and treated as described above for the release media. $^1$H-NMR spectroscopy was used to confirm the chemical structures of the released drugs.

Cytocompatibility Studies.

In vitro cytocompatibility studies were performed by culturing NCTC clone 929 (strain L) mouse areolar fibroblast cells (L929 cells) in cell media (DMEM supplemented with 10% FBS, 1% pen/strep) containing the dissolved diacids (6a and 6b) and polymers (7a and 7b). Polymers and diacids were separately dissolved in dimethyl sulfoxide (DMSO) and diluted with cell media to reach concentrations of 0.10 and 0.05 mg/mL. These solutions were sterilized under UV at λ=254 nm for 900 s (Spectronics Corporation, Westbury, N.Y.) and then allocated to wells in a 96-well plate with 2000 cells/well. DMSO (0.5%) in cell media was used as negative control.

Cell viability was determined using CellTiter 96® Aqueous One Solution Cell Proliferation Assay. After 24 h, 48 h, and 72 h incubation with polymers or diacids, 20 μL of (3-(4,5-dimethylthiazol-2-yl)-5-(3-carboxymethoxyphenyl)-2-(4-sulfophenyl)-2H-tetrazolium) (MTS) reagent was added to each well and further incubated for 2 h at 37° C. The absorbance was then recorded with a microplate reader (Coulter, Boulevard Brea, Calif.) at 492 nm.

Results and Discussion

Synthesis: Polymers Precursors.

Figure 6:
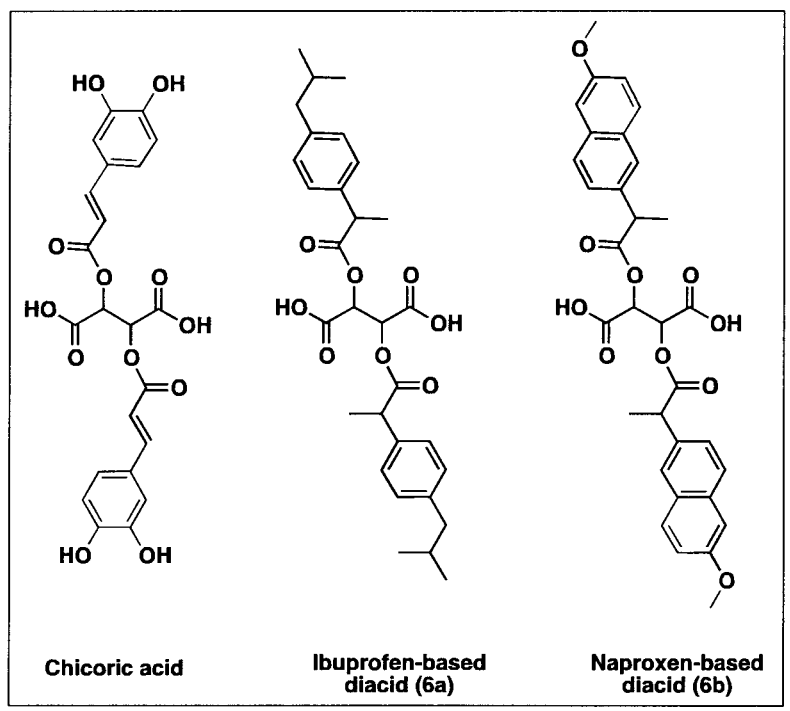
FIG. 6. Chemical structures of chicoric acid, ibuprofen-based diacid (6a), and naproxen-based diacid (6b).

A published procedure (Lamidey, et al., *Helv. Chim. Acta* 2002, 85, 2328-2334) for the synthesis of chicoric acid was adapted to synthesize the polymer precursors ibuprofen- and naproxen-based diacids (6a and 6b, respectively), FIG. 1B. This synthetic procedure was chosen because of the structural similarities between chicoric acid and the diacids 6a and 6b (FIG. 6). Dibenzyl-protected tartaric acid (4) was used for the synthesis of ibuprofen- and naproxen-protected diacids (5a and 5b, respectively), to couple the NSAID (1 or 2) to the hydroxyl groups of the tartrate backbone using EDCI (first step FIG. 1B). Selective deprotection to obtain the diacids 6a and 6b was performed using silane-promoted palladium-mediated hydrogenation (second step FIG. 1B). This debenzylation method is known to preserve sensitive functional groups and the newly formed ester linkages. As expected, compounds 6a and 6b were successfully synthesized using this method. However, the product isolation process was complicated and tedious (comprised of multiple extractions). Therefore, the use of H$_2$ and Pd/C was explored. This common hydrogenation method yielded the pure products (6a and 6b) after an easy isolation comprised of filtration of the Pd/C and evaporation of the solvent and byproducts. All compounds were obtained in high yields (i.e., more than 77%).

Characterization.

Figure 2:
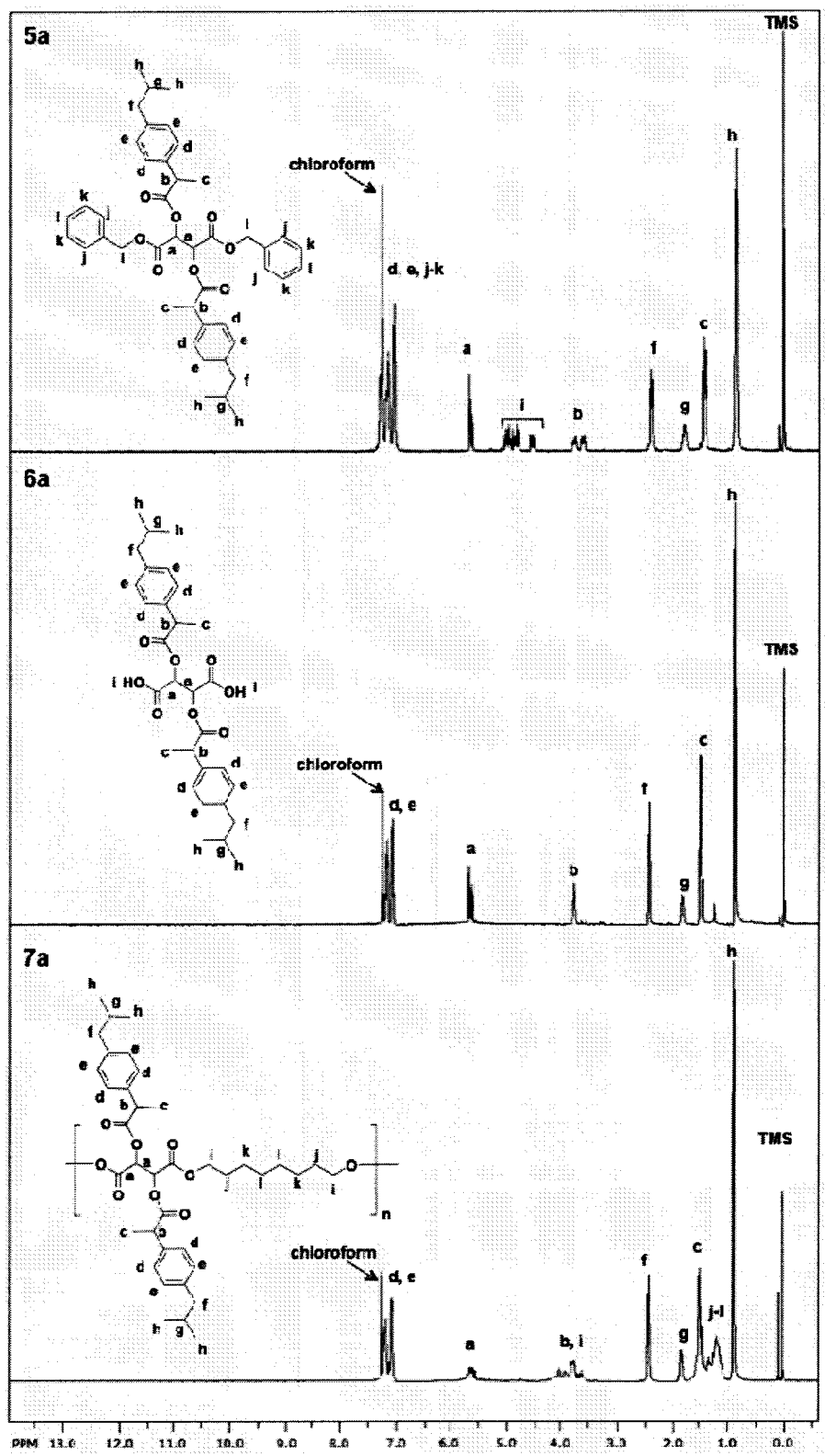
FIG. 2. $^1$H-NMR spectra of compounds 5a (top) and 6a (middle) showing the presence and disappearance of the benzyl protecting groups and polymer 7a (bottom).
Figure 3:
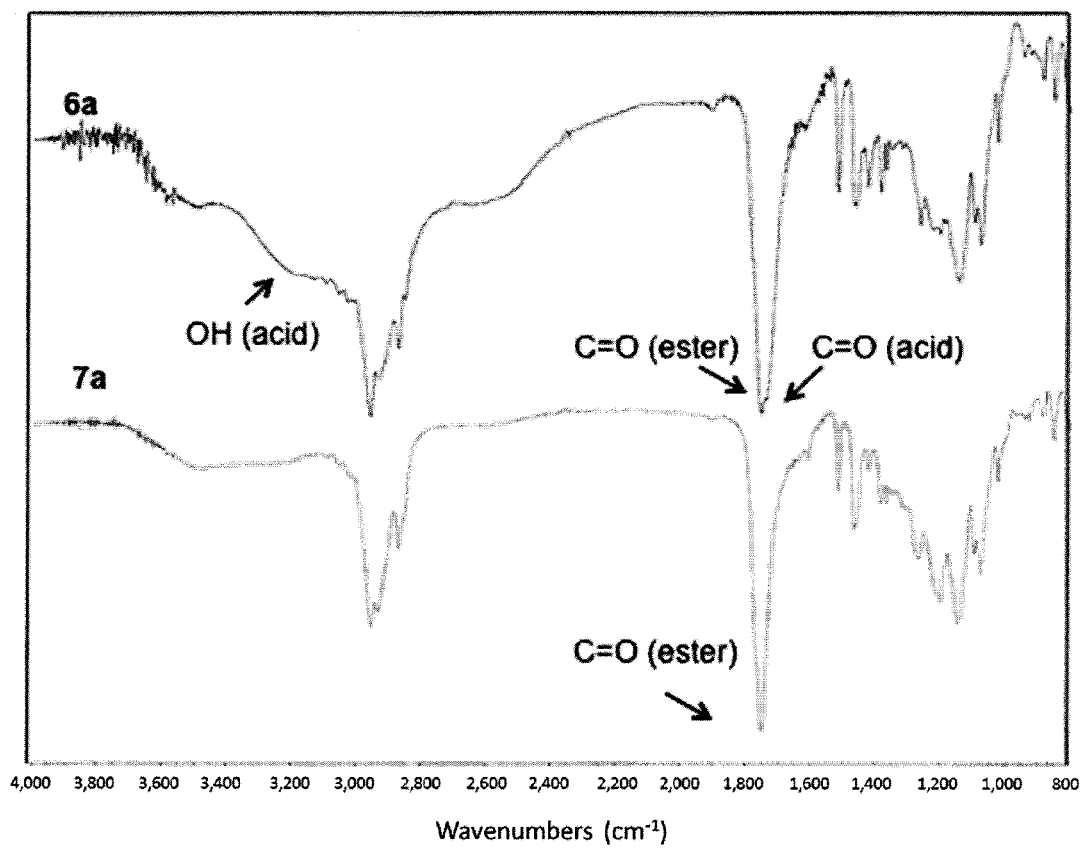
FIG. 3. Infrared spectra of ibuprofen-based diacid 6a (top) and ibuprofen-based polyester 7a (bottom); key stretching frequencies are noted on the spectra.
Figure 7:
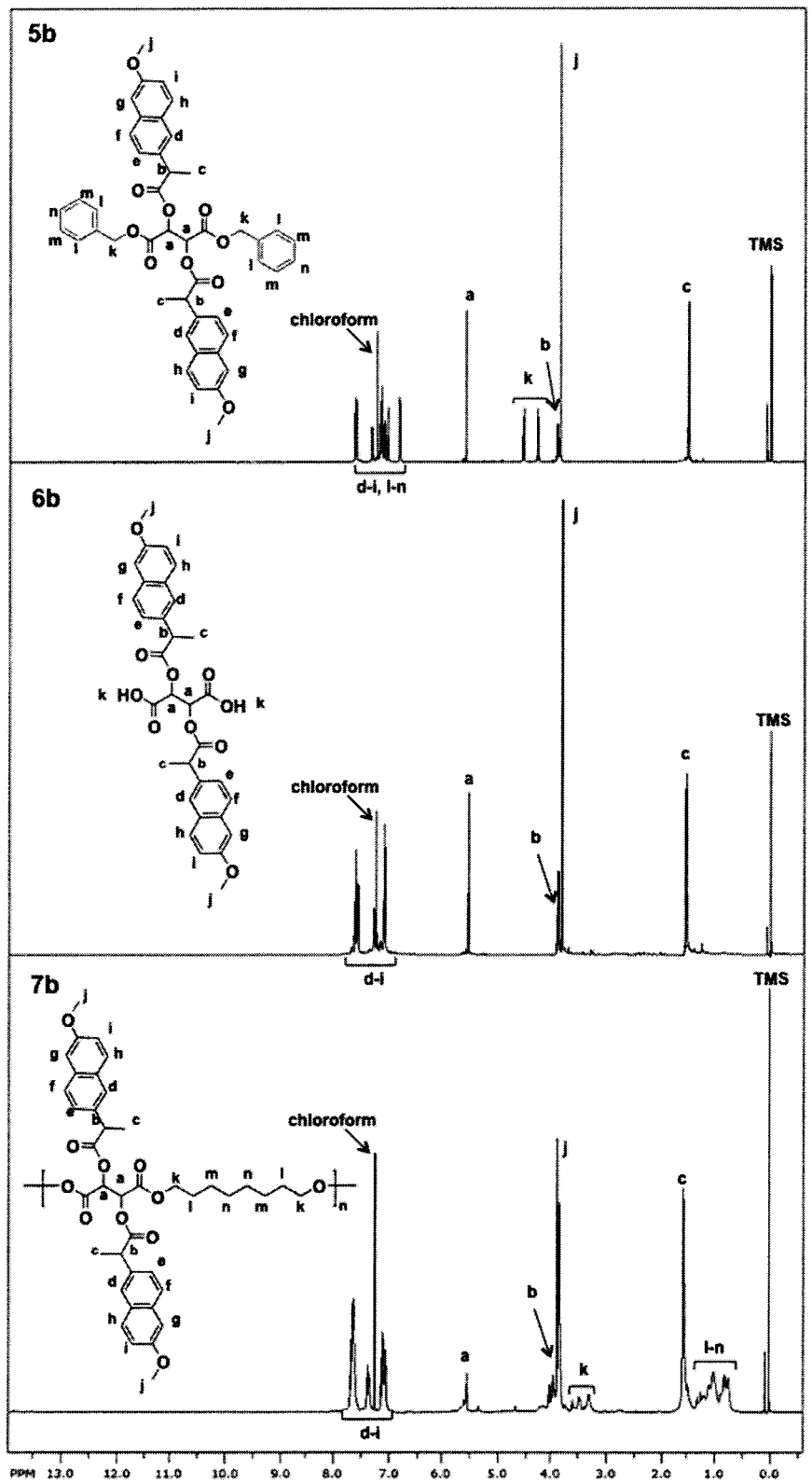
FIG. 7. $^1$H-NMR spectra of compounds 5b (top) and 6b (middle) showing the presence and disappearance of the benzyl protecting groups and polymer 7b (bottom).

The chemical structures of the compounds were confirmed by $^1$H- and $^{13}$C-NMR and IR spectroscopies. FIG. 2 shows the $^1$H-NMR spectra of the ibuprofen-containing compounds 5a and 6a. All the expected peaks are shown in the spectra (FIG. 2 labeled a-k top, a-i middle) with no unexpected peaks observed. The spectra confirms successful coupling of the drug to the tartrate backbone and subsequent deprotection. The debenzylation was successful as demonstrated by the disappearance of the benzylic protons (i-k, FIG. 2 top). For the naproxen-containing compounds 5b and 6b, the debenzylation was also demonstrated by $^1$H-NMR spectra (FIG. 7). The $^{13}$C-NMR spectra showed the presence of all carbons and no extra peaks were observed, also supporting successful deprotection. As further characterization, the IR spectra of 5a and 5b show the formation of the ester bonds by the presence of the ester carbonyls (C=O) at ~1770 and 1750 cm$^{-1}$. The IR spectra of 6a and 6b indicate that deprotection was successful with the presence of the ester carbonyl stretch at ~1760 and terminal carboxylic acid carbonyl stretch at ~1730 cm$^{-1}$ (FIGS. 3 top and 8 top). The molecular weight of the intermediates were confirmed and corresponded to [M+Na]. All compounds were viscous oils or foams and did not display melting points; the decomposition temperatures ranged between 224-294° C. These high decomposition temperatures are important when polymerizing at high temperatures.

Polymers Synthesis and Characterization.

Figure 8:
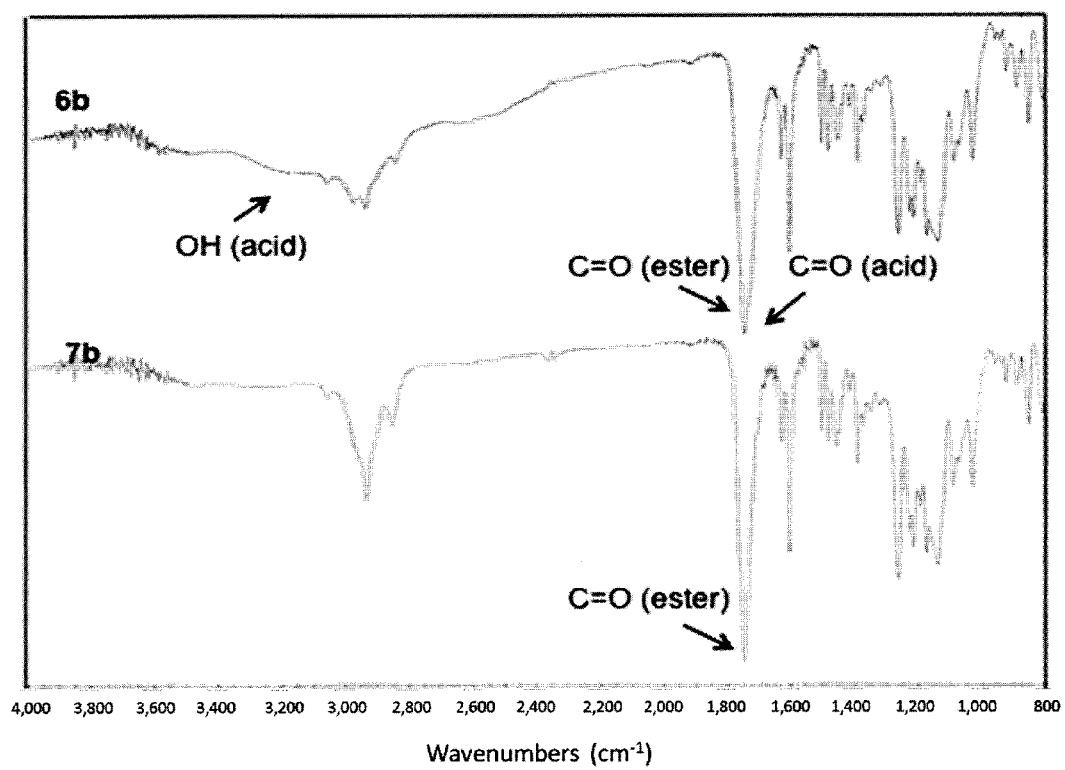
FIG. 8. Infrared spectra of naproxen-based diacid 6b (top) and naproxen-based polyester 7b (bottom); key stretching frequencies are noted on the spectra.

The polyesters was prepared by reacting the diacids 6a and 6b (respectively) with 1,8-octainediol using tin (II) 2-ethylhexanoate as catalyst at 130° C. (step 3 FIG. 1B). Polyesters containing tartaric acid and 1,8-octinediol have been previously reported with tin (II) 2-ethylhexanoate as catalyst (Borzacchiello, et al., *J. Bioact. Compat. Polym.* 2000, 15, 60-71). The 1,8-octainediol is generally regarded as safe and has known bacteriostatic, bactericidal, and preservative properties (Frankenfeld, et al., Exxon Research and Engineering Comapny: United States, 1976, 3, 970). In addition, tin (II) 2-ethylhexanoate the catalyst of choice for many polymerizations due to its low cost, low toxicity, and high efficiency (Storey, et al., *Macromol.* 2002, 35, 1504-1512; Schwach, et al., *Polym. Bull.* 1994, 32, 617-623; Schwach, et al., *Biomaterials* 2002, 23, 993-1002). The $^1$H-NMR spectra for the polymers (7a and 7b) show broadening of the peaks and the presence of all the peaks expected (FIG. 1 bottom and FIG. 7 bottom). The IR spectra of 7a and 7b show the presence of the ester carbonyl at ~1770 and 1750 cm$^{-1}$ (FIGS. 3 and 8, respectively). Polymers with moderate M$_w$ (11,200 and 6,000 Da) and low PDI values (1.2-1.4) were obtained. These polymers decomposed at temperatures above 250° C. and have low T$_g$ values (−17° C. for 7a and 23° C. for 7b).

In Vitro Drug Release.

Figure 4:
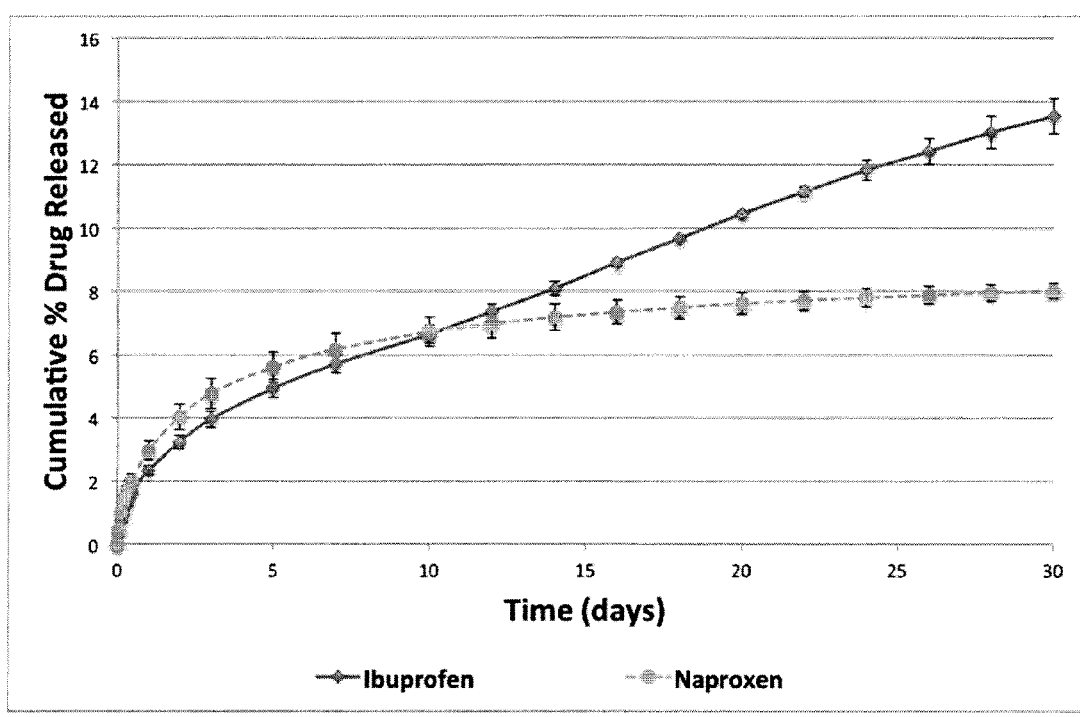
FIG. 4. In vitro ibuprofen (1, filled diamonds) and naproxen (2, filled circles) release profiles from polymers 7a and 7b, respectively (±standard error).

After successfully synthesizing the polymers, their ability to release the free drug was studied in vitro. Polymer samples (7a and 7b) were incubated in buffered media (pH 7.4) mimicking physiological conditions (37° C. and 60 rpm). At predetermined time points, the media was collected and analyzed using HPLC. The retention time (Rt) for 1 was 3.08 min and for 2, 2.40 min, the diacids 6a and 6b had Rt of 4.61 and 3.17 min, respectively. During the studies, oligomers were not detected, and diacid peaks were observed in trace amounts. FIG. 4 shows the in vitro drug release profiles for 1 and 2 during 30 days. No burst release was observed in the degradation profiles; the drugs were released from the respective polymer in a controlled manner. Both drugs were released at approximately the same rate for the first 10 days, as expected due to the structural similarities between the two polymers. Polymer 7a continued to release 1 at a constant rate from day 10 to day 30. However, release of 2 started to plateau after day 10. Further studies will be performed to study the polymer degradation and in vivo drug release mechanisms. After 30 days, polymer 7a released ~14% of 1 and 7b released ~8% of 2 (based on calculated theoretical values). At this rate 100% drug release—and corresponding polymer degradation—is expected in 7 to 12 months.

Figure 9:
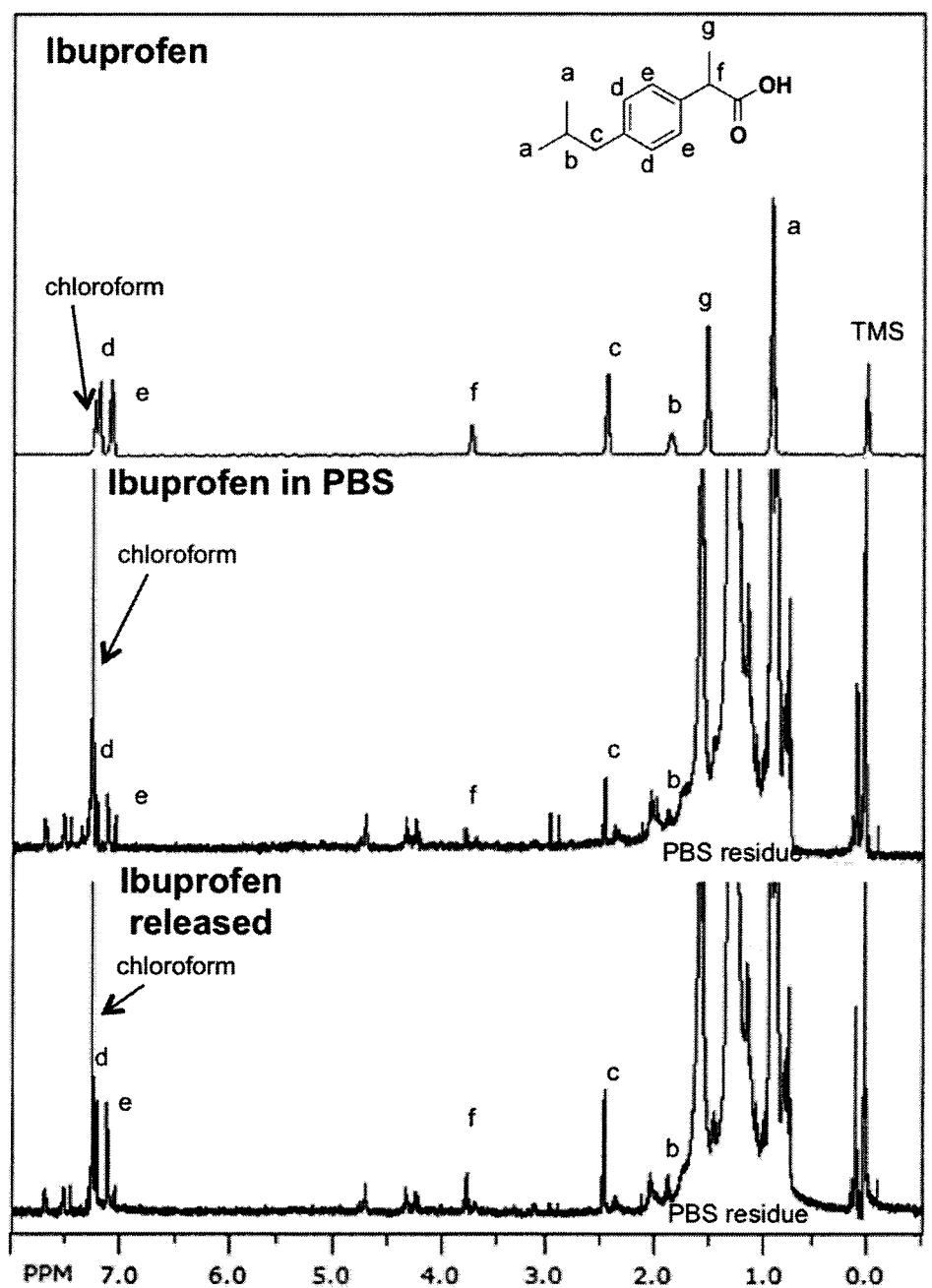
FIG. 9. $^1$H-NMR spectra of free ibuprofen (top), ibuprofen treated in PBS (middle), and ibuprofen released from polymer (bottom), showing the preservation of the chemical structure of the drug.
Figure 10:
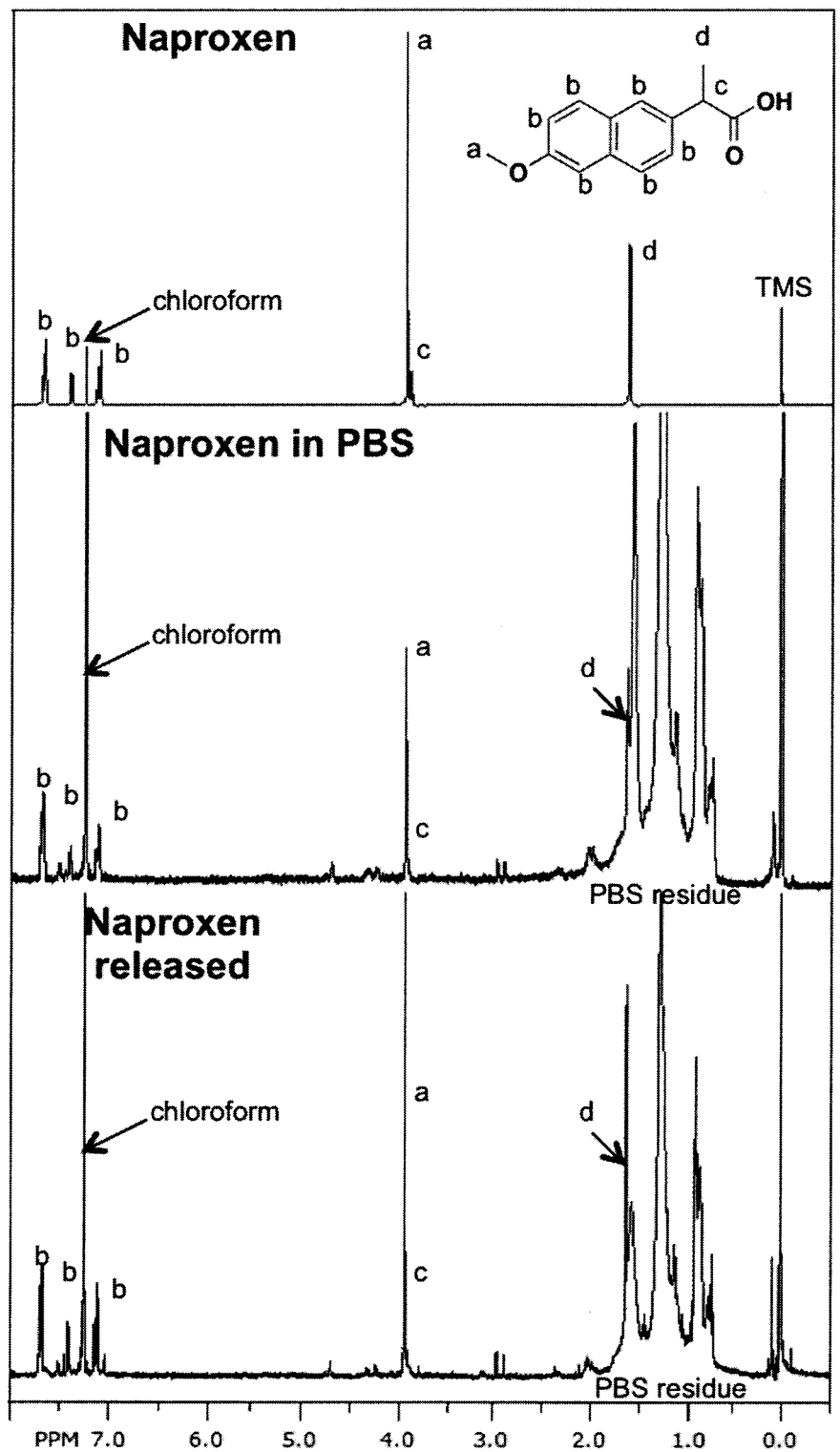
FIG. 10. $^1$H-NMR spectra of free naproxen (top), naproxen treated in PBS (middle), and naproxen released from polymer (bottom), showing the preservation of the chemical structure of the drug.
Figure 11:
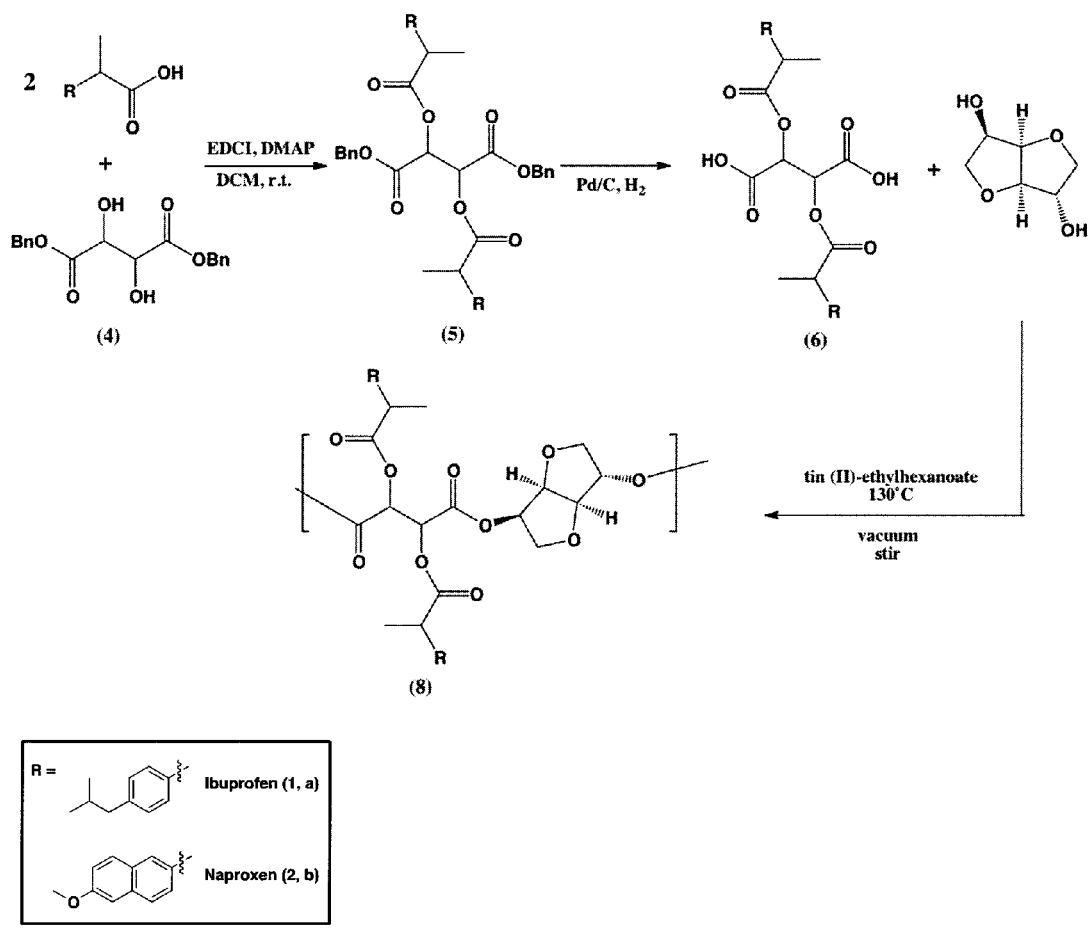
FIG. 11. Synthesis of ibuprofen- and naproxen-protected diacids (5a and 5b, respectively) by coupling of the drug's (1 or 2) carboxylic acids to the hydroxyl groups of the dibenzyl protected tartaric acid (4). Deprotection to yield the diacids (6a and 6b) was performed using palladium-carbon and hydrogen gas and synthesis of ibuprofen- and naproxen-tartaric polymers (8a and 8b) was performed using isosorbide as a diol and tin (II) 2-ethylhexanoate as catalyst. While this synthetic scheme shows the pendant attachment of ibuprofen and naproxen, one skilled in the art may pendantly attach alternative non-steroidal anti-inflammatory agents as described herein.

Following polymerization and in vitro release, the chemical composition of the released bioactives was monitored by $^1$H-NMR spectroscopy. No changes in chemical shifts and integration were observed in comparing the drugs (1 and 2) released at day 5 and the free drugs (FIGS. 9 and 10). These results suggest that the structure of both drugs (1 and 2) were preserved, which implies that the released drugs retain all the properties and activities of the unprocessed drug (FIGS. 9 and 10).

Cell Cytocompatibility Studies.

Figure 5:
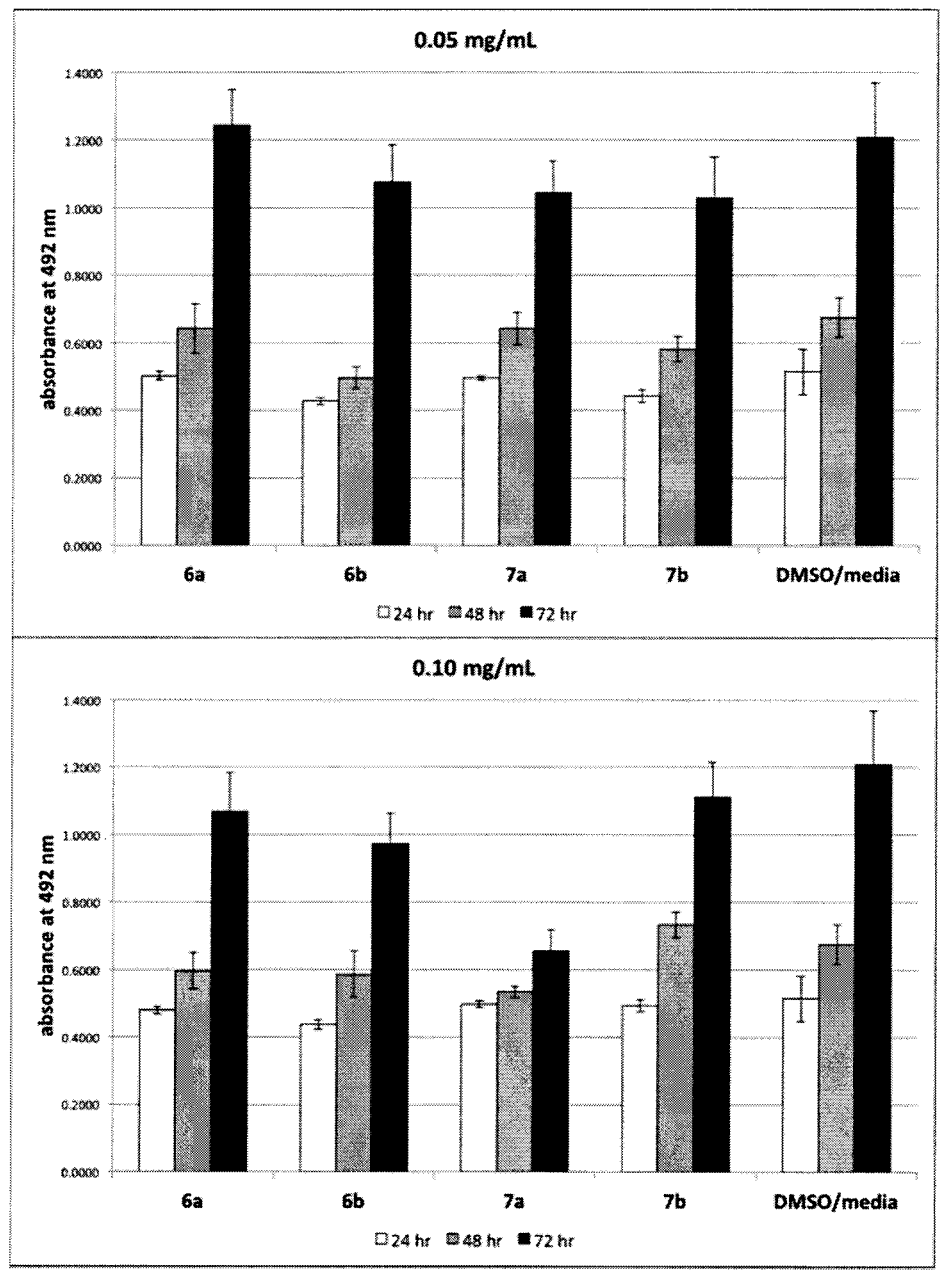
FIG. 5. Normalized L929 cell viability in culture media containing polymers and diacids (top: 0.05 mg/mL; bottom: 0.10 mg/mL) at 24, 48, and 72 h. Data represent mean and standard deviation of six samples.

Cytocompatibility of the diacids and polymers were evaluated using L929 mouse fibroblasts, a commonly used cell type to test toxicity of new biomaterials. The diacids (6a and 6b) and the polymers (7a and 7b), separately, were dissolved in DMSO and then diluted with cell culture media to concentrations of 0.10 and 0.05 mg/mL to mimic late and early polymer degradation, with final DMSO concentration 0.5%. Cell viability was evaluated at 24, 48, and 72 h. FIG. 5 shows cell viability for all samples and the DMSO-containing media control. All samples resulted in normal cell proliferation with the exception that polymer 7a at 0.10 mg/mL resulted in a much lower cell proliferation rate. This data indicates that these materials are mostly cytocompatible within the concentration range tested.

CONCLUSIONS

In this work described herein, the synthesis and characterization of novel biodegradable polyesters comprised of all biocompatible elements (tartaric acid, 1,8-octanediol, and an NSAID (1 or 2)) are presented. With these polymers, the duration of drug release can be prolonged, (more than 1 month) with no burst release. The released drugs retained their chemical structure, suggesting that bioactivity is preserved. These polymers can be used to deliver 1 and 2 in a prolonged and controlled manner, thus have the potential to treat inflammatory diseases. As described herein, other propionic acid-derivative NSAIDs may be incorporated as pendant groups to polyesters and similar in vivo anti-inflammatory activity testing may be performed.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A polyester comprising one or more groups of formula (I):

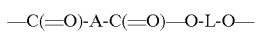 (I)

wherein A is a $C_2$-$C_8$ methylene chain that is covalently linked to two or more residues of a non-steroidal anti-inflammatory; and L is a $C_2$-$C_{10}$ branched or straight chain alkyl.

2. The polyester of claim 1, wherein the $C_2$-$C_8$ methylene chain that is covalently linked to two or more residues of the non-steroidal anti-inflammatory through an ester or amide linkage.

3. The polyester of claim 1 which comprises one or more groups of formula (Ia):

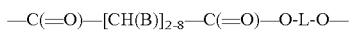 (Ia)

wherein each B is independently a residue of a non-steroidal anti-inflammatory.

4. A polyester according to claim 1, which comprises one or more groups of formula (II):

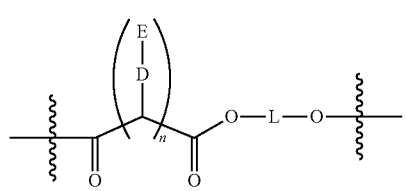 (II)

wherein each D is independently a direct bond, or an ester or amide linkage; each E is independently a residue that will release a non-steroidal anti-inflammatory agent upon hydrolysis of the polymer; n is 2, 3, 4, 5, 6, 7, or 8; and L is a $C_2$-$C_{10}$ branched or straight chain alkyl.

5. The polyester of claim 4 wherein D is —O—.

6. The polyester of claim 5 which comprises one or more groups of formula (IIa):

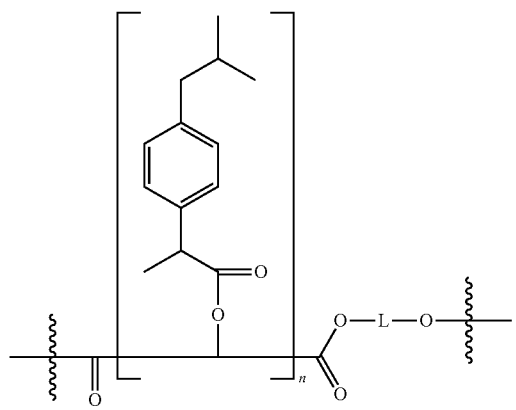 (IIa)

wherein n is 2, 3, 4, 5, 6, 7, or 8.

7. The polyester of claim 5 which comprises one or more groups of formula (IIb):

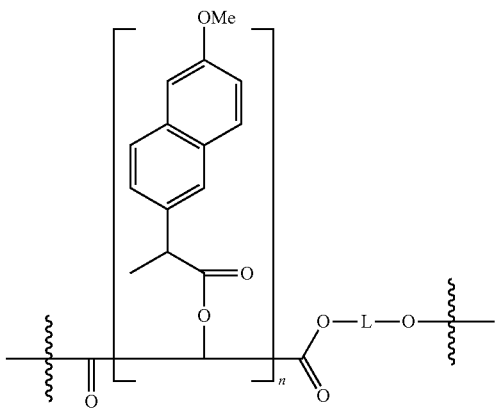 (IIb)

wherein n is 2, 3, 4, 5, 6, 7, or 8.

8. A polyester accordingly to claim 1, which comprises two or more repeating groups of formula (II):

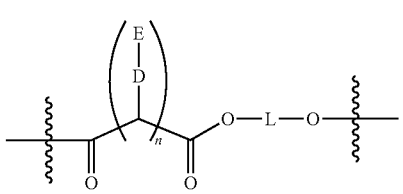 (II)

wherein each D is independently a direct bond, or an ester or amide linkage; each E is independently a residue that will release a non-steroidal anti-inflammatory agent upon hydrolysis of the polymer; n 2, 3, 4, 5, 6, 7, or 8; and L is a $C_2$-$C_{10}$ branched or straight chain alkyl.

9. The polyester of claim 8 which comprises 2-200 repeating groups of formula (II).

10. The polyester of claim 8 which comprises at least 2, 3, 4, 5, 6, 7, 8, or 9 repeating groups of formula (II).

11. The polyester of claim 8 which comprises two or more repeating groups of formula (IIa):

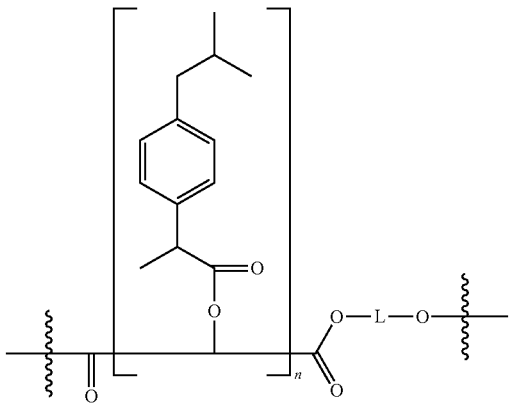 (IIa)

wherein n is 2, 3, 4, 5, 6, 7, or 8.

12. The polyester of claim 8 which comprises two or more repeating groups of formula (IIb):

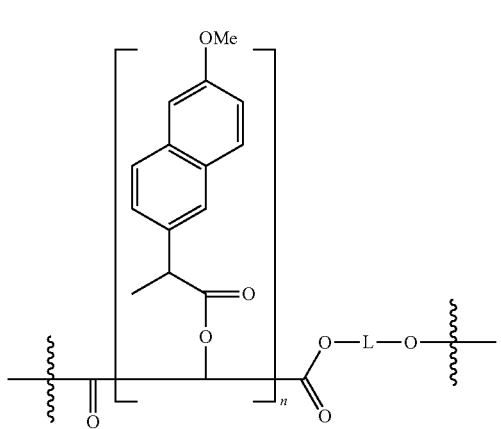

wherein n is 2, 3, 4, 5, 6, 7, or 8.

13. The polyester of claim 1 wherein each non-steroidal anti-inflammatory agent is selected from ibuprofen, naproxen, fenoprofen, ketoprofen, flurbiprofen, suprofen, benoxaprofen, indoprofen, pirprofen, carprofen, loxoprofen, pranoprofen, alminoprofen, salicylic acid, diflunisal, salsalate, oxaprozin, indomethacin, sulindac, etodolac, ketorolac, diclofenac, piroxicam, meloxicam, tenoxican, lornoxicam, isoxicam, mefenamic acid, meclofenamic acid, flufenamic acid, tolfenamic acid, lumiracoxib and licofelone.

14. The polyester of claim 1, wherein L is a $C_2$-$C_{10}$ straight chain alkyl.

15. The polyester of claim 14, wherein L is a $C_4$-$C_8$ straight chain alkyl.

16. The polyester of claim 15, wherein L is a $C_6$ straight chain alkyl.

17. The polyester of claim 1, wherein L is a $C_2$-$C_{10}$ branched chain alkyl.

18. A pharmaceutical composition comprising a polyester as described in claim 1 and a pharmaceutically acceptable carrier.

19. A method to treat pain or inflammation in a mammal, comprising administering a polyester as described in claim 1 to the mammal.

* * * * *